(12) United States Patent
Suzuki et al.

(10) Patent No.: US 7,271,185 B2
(45) Date of Patent: Sep. 18, 2007

(54) OPTICALLY ACTIVE AZOLE DERIVATIVE AND PROCESS FOR PRODUCING THE SAME

(75) Inventors: Tsuneji Suzuki, Sodegaura (JP); Hidetoshi Tsunoda, Sodegaura (JP)

(73) Assignee: Mitsui Chemicals, Inc., Tokyo (JP)

( * ) Notice: Subject to any disclaimer, the term of this patent is extended or adjusted under 35 U.S.C. 154(b) by 239 days.

(21) Appl. No.: 10/503,469

(22) PCT Filed: Feb. 7, 2003

(86) PCT No.: PCT/JP03/01308

§ 371 (c)(1),
(2), (4) Date: Aug. 4, 2004

(87) PCT Pub. No.: WO03/068758

PCT Pub. Date: Aug. 21, 2003

(65) Prior Publication Data

US 2005/0085521 A1 Apr. 21, 2005

(30) Foreign Application Priority Data

Feb. 15, 2002 (JP) .......................... 2002-037966
Aug. 14, 2002 (JP) .......................... 2002-236368

(51) Int. Cl.
*A61K 31/41* (2006.01)
*C07D 249/04* (2006.01)
*C07D 249/08* (2006.01)

(52) U.S. Cl. ...................... 514/359; 514/383; 548/255; 548/262.2

(58) Field of Classification Search ............... 548/255, 548/262.2; 514/359, 383
See application file for complete search history.

(56) References Cited

U.S. PATENT DOCUMENTS

| | | | | |
|---|---|---|---|---|
| 5,004,494 A | * | 4/1991 | Sugavanam et al. | 504/261 |
| 5,204,363 A | * | 4/1993 | Sugavanam et al. | 514/383 |
| 5,648,372 A | | 7/1997 | Naito et al. | |
| 6,300,522 B1 | | 10/2001 | Crosby et al. | |
| 7,060,657 B2 | * | 6/2006 | Hacker et al. | 504/106 |

FOREIGN PATENT DOCUMENTS

EP 753513 A 1/1997
WO 97/31903 A 9/1997

OTHER PUBLICATIONS

Patani et al., "Bioisosterism: A Rational Approach in Drug Design," Chem. Rev., 1996, 96, 3147-3176, especially p. 3157, Table 22.*
Bartroli et al., "New Azole Antifungals. 3. Synthesis and Antifungal Activity of 3-Substituted-4(3H-quinazoliones[1,2]," *J. Med. Chem.*, 1998, pp. 1869-1882, vol. 41, No. 11, American Chemical Society*.
Tasaka et al., "Optically Activity Antifungal Azoles. I. Synthesis and Antifungal Activity of (2R,3R)-2-(2,4-Difluorophenyl)-3-mercapto-1-(1H-1,2,4-triazol-1-yl)-2-butanol and Its Stereoisomers," *Chem. Pharm. Bull.*, Jun. 1993, pp. 1035-1042, vol. 41, No. 6*.

(Continued)

*Primary Examiner*—Rebecca Anderson
*Assistant Examiner*—Susannah Chung
(74) *Attorney, Agent, or Firm*—Buchanan Ingersoll & Rooney PC

(57) ABSTRACT

A method for producing an optically active 2-phenyl-2,3,-dihydroxypropyl azole derivative, which is a useful compound in various fields. An optically active α-hydroxycarboxylic acid derivative represented by general formula (1) is used as a starting material and is allowed to react with an azole acetic acid derivative (2) to produce a new, optically active azole-alkyl ketone derivative (3). Subsequently, a new, optically active azole-methyl alcohol derivative (5) is produced by highly diastereoselective alkylation by an appropriate combination of a protective group and an organometallic reagent (4). Furthermore, the optically active azole-methyl alcohol derivative (5) is selectively deprotected to produce an optically active 2-phenyl-2,3-dihydroxypropyl azole derivative (6)

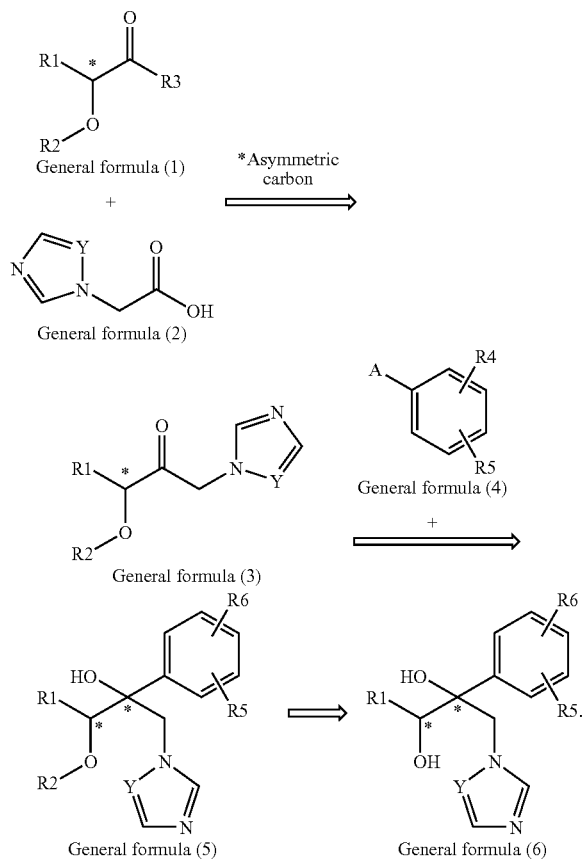

18 Claims, No Drawings

OTHER PUBLICATIONS

Girijavallabhan et al., "Synthesis of the Antifungal Agent SCH 42427[1](SM 9164)," *Bioorganic & Medicinal Chemistry Letters*, 1991, pp. 349-352, vol. 1, No. 7, Pergamon Press plc, Great Britain*.

Adam et al., "Synthesis of Optically Active α-Hydroxycarbonyl Compounds by (Salen)Mn(III)-Catalyzed Oxidation of Silyl Enol Ethers and Silyl Ketene Acetals," *Tetrahedron Letters*, 1996, pp. 6531-6534, vol. 37, No. 36, Elsevier Science Ltd., Great Britain*.

"New Antifungal Agents," *Iyaku Journal*, 2001, pp. 115-119 (2105-2109), vol. 37, No. 7 (English abstract).

* cited by examiner

OPTICALLY ACTIVE AZOLE DERIVATIVE AND PROCESS FOR PRODUCING THE SAME

TECHNICAL FIELD

The present invention relates to a new, simple method for producing an optically active 2-phenyl-2,3,-dihydroxypropyl azole derivative, which is an important compound in many fields such as medicines and agricultural chemicals.

BACKGROUND ART

Recently, immunocompromised patients due to infection with, for example, AIDS and patients who have a low immunity due to highly developed medical treatment or due to an increase in old people have been increasing. Unfortunately, these phenomena increase the livelihood of fungal infections typified by opportunistic infection. A great deal of attention in medical fields should be paid to deep-seated fungal infections such as candidiasis and aspergillosis, because these fungal infections often cause serious life-threatening problems to, in particular, patients who have a low immunity. Azole antifungal agents typified by fluconazole have been widely used as a curative medicine for these infections. In recent years, however, the emergence of resistant strains and insufficient basic behavior of the known antifungal agents have been identified. Therefore, the development of a curative medicine that is effective for a wider range of strains and is more powerful is desirable (Iyaku Journal, Vol. 37 (7), PP. 115-119, 2001).

According to a recent tendency in the development of azole antifungal agents, antifungal agents have a more complex molecular structure. In particular, a significant technical challenge is how to effectively achieve a structure that includes an asymmetric carbon bonded to an azole methyl group and an adjoining asymmetric carbon (J. Med. Chem., Vol. 41, PP. 1869-1882, 1998). In terms of industrial production, a stable method for producing an antifungal agent inexpensively has not been established so far.

The known processing technology will now be described.

In order to produce the adjoining asymmetric portion, an α-hydroxyphenyl ketone derivative is generally used as the intermediate and the ketone group is subjected to diastereoselective carbon-increasing epoxidation (Chem. Pharm. Bull., Vol. 41 (6), PP. 1035-1042, 1993). Unfortunately, in terms of industrial production, the known method has the following serious disadvantages: (1) The diastereoselectivity in the method is as low as about 4:1. (2) The yield in the isolation of the desired isomer is low. (3) The isolation and the purification require very complex steps. (4) The method causes racemization under some reaction conditions. In addition, a method for producing the α-hydroxyphenyl ketone derivative also includes complex steps (Bioorg. Med. Chem. Lett., Vol. 1 (7), PP. 349-352, 1991), and requires an expensive reaction reagent such as an asymmetric catalyst (Tetrahedron Letters, Vol. 37 (36), PP. 6531-6534, 1996). Thus, the known method is not a satisfactory method in terms of industrial production. Recently, a new, improved method has been reported in which L-alanine is used as the starting material (U.S. Pat. No. 6,300,522). According to this method, however, the fundamental problem is still not solved, because the method also uses an α-hydroxyphenyl ketone derivative as the intermediate. Therefore, the method is still not a satisfactory method in terms of industrial production.

As described above, despite the demand for the development of a new, more useful azole antifungal agent, in terms of industrial production, a stable method for producing an antifungal agent inexpensively has not been established in the known processing technology, because the azole antifungal agent is an optically active compound having two asymmetric carbons. Accordingly, the prompt development of a new, more effective method is desirable regarding the intermediate compound.

DISCLOSURE OF INVENTION

It is an object of the present invention to provide a method for producing an optically active 2-phenyl-2,3,-dihydroxypropyl azole derivative, which is a useful compound in the field of medicines and agricultural chemicals, and is, in particular, a significantly important intermediate in the step of producing an optically active azole antifungal agent. According to the method of the present invention, in terms of industrial production, the derivative can be produced inexpensively and stably by simple steps. It is an object of the present invention to provide new intermediates produced in some steps in the method.

As a result of intensive study to achieve the object, the present inventors have found that it is possible to produce a new, optically active azole-alkyl ketone derivative that is a significantly important intermediate of medicines and agricultural chemicals by using an optically active α-hydroxycarboxylic acid derivative as the starting material and by allowing the material to react with an azole acetic acid derivative. The present inventors have also found a highly diastereoselective reaction in the alkylation of the new, optically active azole-alkyl ketone derivative to produce a new, optically active azole-methyl alcohol derivative that is a significantly important intermediate of medicines and agricultural chemicals. According to the diastereoselective reaction, anti or syn configuration can be arbitrarily controlled depending on the selection of the protective group and the reaction conditions. Furthermore, the present inventors have found a new route for producing an optically active 2-phenyl-2,3-dihydroxypropyl azole derivative, which is a significantly important intermediate of medicines and agricultural chemicals, by selectively deprotecting the new optically active azole-methyl alcohol derivative. According to this reaction, a compound having the desired configuration can be selectively produced with high optical purity without racemization. In particular, the present inventors have found the following method: An inexpensive lactic acid derivative is used as the optically active α-hydroxycarboxylic acid derivative. A silyl group is used as the protective group to produce a new, optically active silyloxy-azole-alkyl ketone derivative, which is an intermediate. The intermediate is then subjected to alkylation with significantly high syn selectivity to produce a new, optically active silyloxy-azole-methyl alcohol derivative. The optically active silyloxy-azole-methyl alcohol derivative is a significantly important intermediate to produce an optically active azole antifungal agent. Accordingly, a 2-phenyl-2,3-dihydroxypropyl azole derivative having the desired configuration can be produced with high optical purity. According to this method, the 2-phenyl-2,3-dihydroxypropyl azole derivative, which is a significantly important intermediate to produce the optically active azole antifungal agent, can be produced inexpensively and stably by simple steps, in terms of industrial production.

The present invention is based on this fact found by the inventors.

The present invention includes following Items [1] to [14].

[1] A method for producing an optically active 2-phenyl-2,3-dihydroxypropyl azole derivative represented by general formula (6):

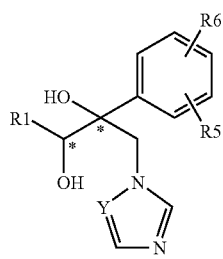

(wherein R1 represents a substituted or unsubstituted alkyl group, a substituted or unsubstituted aralkyl group, a substituted or unsubstituted aryl group, or a substituted or unsubstituted heterocyclic group; each of R5 and R6 independently represents a halogen atom, an alkyloxycarbonyl group, an aryloxycarbonyl group, a substituted or unsubstituted amino group, a substituted or unsubstituted amido group, a substituted or unsubstituted alkyl group, a substituted or unsubstituted alkyloxy group, a substituted or unsubstituted aralkyl group, a substituted or unsubstituted aralkyloxy group, a substituted or unsubstituted phenyl group, a substituted or unsubstituted phenoxy group, a substituted or unsubstituted heterocyclic group, or a substituted or unsubstituted heterocyclicoxy group; symbol * represents an asymmetric carbon having an R configuration or an S configuration; and Y represents a carbon atom or a nitrogen atom) includes the steps of allowing an optically active α-hydroxycarboxylic acid derivative represented by general formula (1):

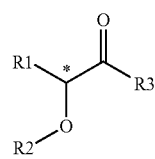

(wherein R1 and symbol * are as defined above; R2 represents an ether protective group, an acetal protective group, or a silyl protective group, which is a protective group for a hydroxyl group; R3 represents a hydroxyl group, a halogen atom, a substituted or unsubstituted acyl group, a substituted or unsubstituted carbonate group, a substituted or unsubstituted alkyloxy group, a substituted or unsubstituted aralkyloxy group, a substituted or unsubstituted phenoxy group, or a substituted or unsubstituted amino group) to react with an azole acetic acid derivative represented by general formula (2):

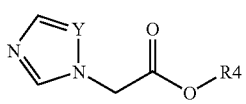

(wherein R4 represents a hydrogen atom, a substituted or unsubstituted alkyl group, an alkali metal, or an alkaline earth metal salt; and Y is as defined above) under a basic condition to produce an azole-methyl ketone derivative represented by general formula (3):

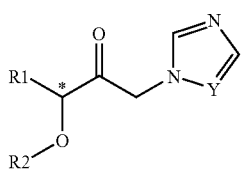

(wherein R1, R2, symbol *, and Y are as defined above); allowing the optically active azole-methyl ketone derivative represented by general formula (3) to diastereoselectively react with a phenyl metallic reagent represented by general formula (4):

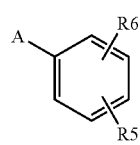

(wherein R5 and R6 are as defined above; A represents Li, MgX, ZnX, TiX₃, Ti(OR7)₃, CuX, or CuLi, {wherein X represents a halogen atom, and R7 represents a substituted or unsubstituted alkyl group}) to produce an optically active azole-methyl alcohol derivative represented by general formula (5):

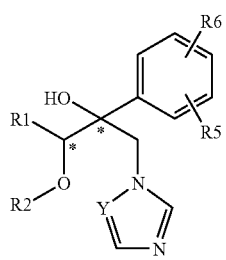

(wherein R1, R2, R5, R6, symbol *, and Y are as defined above); and selectively deprotecting the protective group R2 for a hydroxyl group of the optically active azole-methyl alcohol derivative represented by general formula (5).

[2] A method for producing an azole-methyl ketone derivative represented by general formula (3) (wherein R1, R2, Y, and symbol * are as defined above) includes allowing an α-hydroxycarboxylic acid derivative represented by general formula (1) (wherein R1, R2, R3, and symbol * are as defined above) to react with an azole acetic acid derivative represented by general formula (2) (wherein R4 and Y are as defined above) under a basic condition.

[3] A method for producing an optically active azole-methyl alcohol derivative represented by general formula (5) (wherein R1, R2, R5, R6, Y, and symbol * are as defined above) includes allowing an optically active azole-methyl ketone derivative represented by general formula (3) (wherein R1, R2, Y, and symbol * are as defined above) to diastereoselectively react with a phenyl metallic reagent represented by general formula (4) (wherein R5, R6, A, X, and R7 are as defined above).

[4] A method for producing an optically active azole-methyl alcohol derivative represented by general formula (5) (wherein R1, R2, R5, R6, Y, and symbol * are as defined above) includes allowing an optically active azole-methyl ketone derivative represented by general formula (3) (wherein R1, R2, Y, and symbol * are as defined above) to anti-selectively react with a phenyl metallic reagent represented by general formula (4) (wherein R5, R6, A, X, and R7 are as defined above).

[5] A method for producing an optically active azole-methyl alcohol derivative represented by general formula (5) (wherein R1, R2, R5, R6, Y, and symbol * are as defined above) includes allowing an optically active azole-methyl ketone derivative represented by general formula (3) (wherein R1, R2, Y, and symbol * are as defined above) to syn-selectively react with a phenyl metallic reagent represented by general formula (4) (wherein R5, R6, A, X, and R7 are as defined above).

[6] A method for producing an optically active 2-phenyl-2,3-dihydroxypropyl azole derivative represented by general formula (6) (wherein R1, R5, R6, Y, and symbol * are as defined above) includes selectively deprotecting the protective group R2 for a hydroxyl group of an optically active azole-methyl alcohol derivative represented by general formula (5) (wherein R1, R2, R5, R6, Y, and symbol * are as defined above).

[7] The method according to any one of Item [1] to Item [6] wherein R1 is a methyl group, and each of R5 and R6 is a fluorine or chlorine atom.

[8] An optically active azole-methyl ketone represented by general formula (3) (wherein R1, R2, Y, and symbol * are as defined above).

[9] The optically active azole-methyl ketone according to Item [8], wherein R1 is a methyl group.

[10] The optically active azole-methyl ketone according to Item [9], wherein R2 is a silyl protective group.

[11] An optically active azole-methyl alcohol derivative represented by general formula (5) (wherein R1, R5, R6, Y, and symbol * are as defined above), wherein R2 is a silyl protective group.

[12] The optically active azole-methyl alcohol derivative according to Item [11], wherein R1 is a methyl group.

[13] The optically active azole-methyl alcohol derivative according to Item [12], wherein each of R5 and R6 is a halogen atom.

[14] The optically active azole-methyl alcohol derivative according to Item [13], wherein Y is a nitrogen atom.

BEST MODE FOR CARRYING OUT THE INVENTION

The compounds of the present invention will now be described in detail.

According to the present invention, "a substituted or unsubstituted alkyl group" represents an alkyl group in which any position of the alkyl group may be substituted. Examples of the alkyl group include methyl, ethyl, isopropyl, tert-butyl, pentyl, hexyl, octyl, decyl, and allyl groups. Examples of the substituent include; hydroxyl group; alkoxy groups such as methoxy, benzyloxy, and methoxyethoxy groups; a phenoxy group; a nitro group; an amino group; an amido group; a carboxyl group; alkoxycarbonyl groups; a phenoxycarbonyl group; and halogen atoms such as fluorine, chlorine, bromine, and iodine atoms.

According to the present invention, "a substituted or unsubstituted aralkyl group" represents an aralkyl group in which any position of the aralkyl group may be substituted. Examples of the aralkyl group include benzyl, naphthylmethyl, phenylethyl, and 9-fluorenylmethyl groups. Examples of the substituent include alkyl groups such as methyl, tert-butyl, and benzyl groups; cycloalkyl groups such as cyclopropane, cyclopentane, and cyclohexane; a phenyl group; hydroxyl group; alkoxy groups such as methoxy, benzyloxy, and methoxyethoxy groups; a phenoxy group; a nitro group; an amino group; an amido group; a carboxyl group; alkoxycarbonyl groups; a phenoxycarbonyl group; and halogen atoms such as fluorine, chlorine, bromine, and iodine atoms.

According to the present invention, "a substituted or unsubstituted aryl group" represents an aryl group in which any position of the aryl group may be substituted. Examples of the aryl group include phenyl, naphthyl, anthracenyl, fluorenyl, and phenanthryl groups. Examples of the substituent include alkyl groups such as methyl, tert-butyl, and benzyl groups; cycloalkyl groups such as cyclopropane, cyclopentane, and cyclohexane; a phenyl group; hydroxyl group; alkoxy groups such as methoxy, benzyloxy, and methoxyethoxy groups; a phenoxy group; a nitro group; an amino group; an amido group; a carboxyl group; alkoxycarbonyl groups; a phenoxycarbonyl group; and halogen atoms such as fluorine, chlorine, bromine, and iodine atoms.

According to the present invention, "a substituted or unsubstituted heterocyclic group" represents a heterocyclic group in which any position of the heterocyclic group having a heteroatom such as oxygen, nitrogen, and sulfur atoms may be substituted. Examples of the heterocyclic group include tetrahydropyranyl, tetrahydrofuranyl, tetrahydrothienyl, piperidyl, morpholinyl, piperazinyl, pyrrolyl, furyl, thienyl, pyridyl, furfuryl, thenyl, pyridylmethyl, pyrimidyl, pyrazyl, imidazolyl, imidazolylmethyl, indolyl, indolylmethyl, isoquinolyl, quinolyl, and thiazolyl groups. Examples of the substituent include alkyl groups such as methyl, tert-butyl, and benzyl groups; cycloalkyl groups such as cyclopropane, cyclopentane, and cyclohexane; a phenyl group; hydroxyl group; alkoxy groups such as methoxy, benzyloxy, and methoxyethoxy groups; a phenoxy group; a nitro group; an amino group; an amido group; a carboxyl group; alkoxycarbonyl groups; a phenoxycarbonyl group; and halogen atoms such as fluorine, chlorine, bromine, and iodine atoms.

According to the present invention, "an ether protective group which is a protective group for a hydroxyl group" represents a protective group that protects the hydroxyl group, and the protective group having an ether bond. Examples of the protective group include methyl, ethyl, tert-butyl, octyl, allyl, benzyl, p-methoxybenzyl, fluorenyl, trityl, and benzhydryl groups.

According to the present invention, "an acetal protective group" represents a protective group that protects the hydroxyl group, and the protective group having an acetal bond. Examples of the protective group include methoxymethyl, ethoxyethyl, methoxyethoxymethyl, tetrahydropyranyl, and tetrahydrofuranyl groups.

According to the present invention, "a silyl protective group" represents a protective group that protects the hydroxyl group, and the protective group having a silyloxy bond. Examples of the protective group include trimethylsilyl, triethylsilyl, tert-butyldimethylsilyl, and tert-butyldiphenylsilyl groups.

According to the present invention, examples of "a halogen atom" include fluorine, chlorine, bromine, and iodine atoms.

According to the present invention, "a substituted or unsubstituted acyl group" represents an acyl group in which any position of the acyl group may be substituted. Examples of the acyl group include formyl, acetyl, propionyl, pivaloyl, and benzoyl groups. Examples of the substituent include alkyl groups such as methyl, tert-butyl, and benzyl groups; cycloalkyl groups such as cyclopropane, cyclopentane, and cyclohexane; a phenyl group; hydroxyl group; alkoxy groups such as methoxy, benzyloxy, and methoxyethoxy groups; a phenoxy group; a nitro group; an amino group; an amido group; a carboxyl group; alkoxycarbonyl groups; a phenoxycarbonyl group; and halogen atoms such as fluorine, chlorine, bromine, and iodine atoms.

According to the present invention, "a substituted or unsubstituted carbonate group" represents a carbonate group in which any position of the carbonate group may be substituted. Examples of the carbonate group include methyl carbonate, ethyl carbonate, isopropyl carbonate, and benzyl carbonate groups. Examples of the substituent include alkyl groups such as methyl, tert-butyl, and benzyl groups; cycloalkyl groups such as cyclopropane, cyclopentane, and cyclohexane; a phenyl group; hydroxyl group; alkoxy groups such as methoxy, benzyloxy, and methoxyethoxy groups; a phenoxy group; a nitro group; an amino group; an amido group; a carboxyl group; alkoxycarbonyl groups; a phenoxycarbonyl group; and halogen atoms such as fluorine, chlorine, bromine, and iodine atoms.

According to the present invention, "a substituted or unsubstituted alkyloxy group" represents an alkyloxy group in which any position of the alkyloxy group may be substituted. Examples of the alkyloxy group include methoxy, ethoxy, isopropoxy, tert-butoxy, pentyloxy, hexyloxy, octyloxy, decyloxy, and allyloxy groups. Examples of the substituent include hydroxyl group; alkoxy groups such as methoxy, benzyloxy, and methoxyethoxy groups; a phenoxy group; a nitro group; an amino group; an amido group; a carboxyl group; alkoxycarbonyl groups; a phenoxycarbonyl group; and halogen atoms such as fluorine, chlorine, bromine, and iodine atoms.

According to the present invention, "a substituted or unsubstituted aralkyloxy group" represents an aralkyloxy group in which any position of the aralkyloxy group may be substituted. Examples of the aralkyloxy group include benzyloxy, naphthylmethyloxy, phenylethyloxy, and 9-fluorenylmethyloxy groups. Examples of the substituent include alkyl groups such as methyl, tert-butyl, and benzyl groups; cycloalkyl groups such as cyclopropane, cyclopentane, and cyclohexane; a phenyl group; hydroxyl group, alkoxy groups such as methoxy, benzyloxy, and methoxyethoxy groups; a phenoxy group; a nitro group; an amino group; an amido group; a carboxyl group; alkoxycarbonyl groups; a phenoxycarbonyl group; and halogen atoms such as fluorine, chlorine, bromine, and iodine atoms.

According to the present invention, "a substituted or unsubstituted phenoxy group" represents a phenoxy group in which any position of the phenoxy group may be substituted. Examples of the substituent include alkyl groups such as methyl, tert-butyl, and benzyl groups; cycloalkyl groups such as cyclopropane, cyclopentane, and cyclohexane; a phenyl group; hydroxyl group; alkoxy groups such as methoxy, benzyloxy, and methoxyethoxy groups; a phenoxy group; a nitro group; an amino group; an amido group; a carboxyl group; alkoxycarbonyl groups; a phenoxycarbonyl group; and halogen atoms such as fluorine, chlorine, bromine, and iodine atoms.

According to the present invention, "a substituted or unsubstituted amino group" represents an amino group in which any position of the amino group may be substituted. Examples of the substituent include alkyl groups such as methyl, tert-butyl, and benzyl groups; cycloalkyl groups such as cyclopropane, cyclopentane, and cyclohexane; and a phenyl group.

According to the present invention, examples of "an alkali metal" include lithium, sodium, potassium, rubidium, and cesium.

According to the present invention, "an alkaline earth metal salt" represents a salt of, for example, magnesium, calcium, strontium, barium, or beryllium. Examples of the alkaline earth metal salt include magnesium halides, magnesium alkoxides, calcium halides, calcium alkoxides, strontium halides, barium halides, and beryllium halides. In more detail, examples of the alkaline earth metal salt include magnesium salts such as —MgCl, —MgBr, —MgOMe, and —MgOEt; calcium salts such as —CaCl, —CaBr, —CaOMe, and —CaOEt; and barium salts such as —BaCl, —BaBr, —BaOMe, and —BaOEt. Two molecules of an azole acetic acid derivative may form a single alkaline earth metal salt.

According to the present invention, examples of "an alkyloxycarbonyl group" include methoxycarbonyl, ethoxycarbonyl, and tert-butoxycarbonyl groups.

According to the present invention, examples of "an aryloxycarbonyl group" include phenoxycarbonyl and naphthyloxycarbonyl groups.

According to the present invention, "a substituted or unsubstituted amido group" represents an amido group in which any position of the amido group may be substituted. Examples of the substituent include alkyl groups such as methyl, tert-butyl, and benzyl groups; cycloalkyl groups such as cyclopropane, cyclopentane, and cyclohexane; and a phenyl group.

According to the present invention, "a substituted or unsubstituted heterocyclicoxy group" represents a heterocyclicoxy group in which any position of the heterocyclicoxy group may be substituted. Examples of the heterocyclicoxy group include tetrahydropyranyloxy, tetrahydrofuranyloxy, tetrahydrothienyloxy, piperidyloxy, morpholinyloxy, piperazinyloxy, pyrrolyloxy, furyloxy, thienyloxy, pyridyloxy, furfuryloxy, thenyloxy, pyridylmethyloxy, pyrimidyloxy, pyrazyloxy, imidazolyloxy, imidazolylmethyloxy, indolyloxy, indolylmethyloxy, isoquinolyloxy, quinolyloxy, and thiazolyloxy groups. Examples of the substituent include alkyl groups such as methyl, tert-butyl, and benzyl groups; cycloalkyl groups such as cyclopropane, cyclopentane, and cyclohexane; a phenyl group; hydroxyl group; alkoxy groups such as methoxy, benzyloxy, and methoxyethoxy groups; a phenoxy group; a nitro group; an amino group; an amido group; a carboxyl group; alkoxycarbonyl groups; a phenoxycarbonyl group; and halogen atoms such as fluorine, chlorine, bromine, and iodine atoms.

According to the present invention, "allowing the compound represented by general formula (3) to diastereoselectively react with the reagent represented by general formula (4) to produce the compound represented by general formula (5)" means to selectively produce a new asymmetric carbon adjoining an asymmetric carbon in general formula (3). The term "anti-selectively" has the following meaning. In a plane on which a carbon chain is disposed in a zigzag, a hydroxyl group is produced at the opposite side of the R2O-group bonded to the optically active carbon atom. The term "syn-selectively" has the following meaning. In a plane on which a carbon chain is disposed in a zigzag, a hydroxyl group is produced at the same side of the R2O-group bonded to the optically active carbon atom. In other words, the selectivity represented by "anti-selectively" is the diastereoselectivity represented by general formula (7).

As shown in general formula (7), an (S)-enantiomer produces an (S, R)-diastereomer, and an (R)-enantiomer produces an (R, S)-diastereomer.

The selectivity represented by "syn-selectively" is the diastereoselectivity represented by general formula (8).

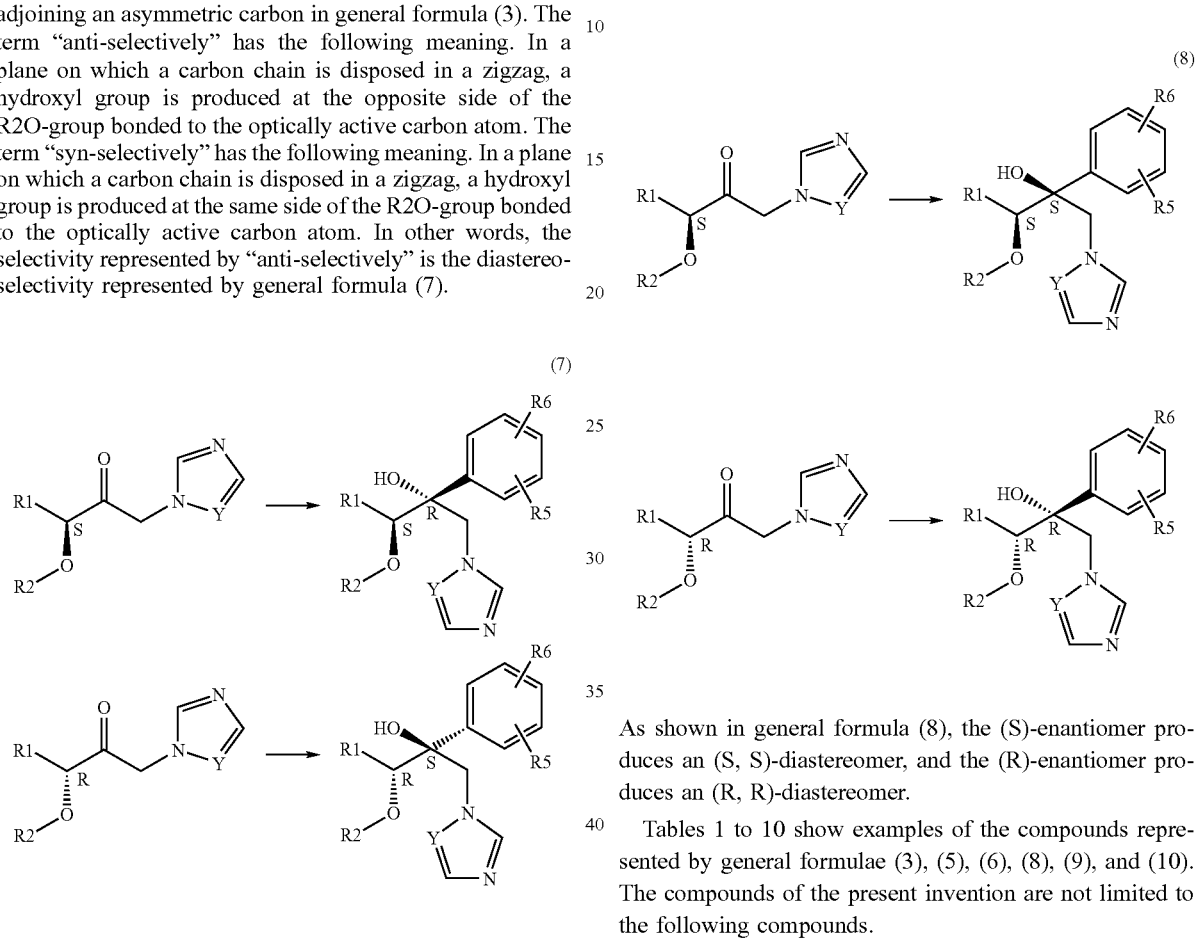

As shown in general formula (8), the (S)-enantiomer produces an (S, S)-diastereomer, and the (R)-enantiomer produces an (R, R)-diastereomer.

Tables 1 to 10 show examples of the compounds represented by general formulae (3), (5), (6), (8), (9), and (10). The compounds of the present invention are not limited to the following compounds.

TABLE 1

General formula (3)

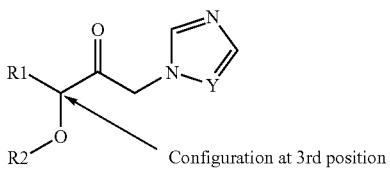

Configuration at 3rd position

| Compound number | Configuration at 3rd position | R1 | R2 | Y |
|---|---|---|---|---|
| R101 | R | $CH_3$— | $CH_3$— | N |
| R102 | R | $(CH_3)_2CH$— | $CH_3$— | N |
| R103 | R | $PhCH_2$— | $CH_3$— | N |
| R104 | R | $(CH3)_3C$— | $CH_3$— | C |
| R105 | R | $PhCH_2OCH_2$— | $CH_3$— | N |
| R106 | R | $CH_3OC(O)CH_2$— | $CH_3$— | N |
| R107 | R | $ClCH_2$— | $CH_3$— | N |
| R108 | R | $H_2NC(O)CH_2CH_2$— | $CH_3$— | C |

TABLE 1-continued

General formula (3)

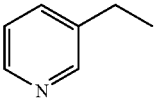

| Compound number | Configuration at 3rd position | R1 | R2 | Y |
|---|---|---|---|---|
| R109 | R | 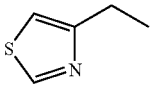 | CH₃— | N |
| R110 | R | 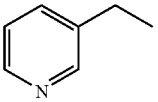 | CH₃— | N |
| R111 | R | CH₃— | PhCH₂— | N |
| R112 | R | (CH₃)₂CH— | PhCH₂— | N |
| R113 | R | PhCH₂— | PhCH₂— | C |
| R114 | R | (CH3)₃C— | PhCH₂— | N |
| R115 | R | PhCH₂OCH₂— | PhCH₂— | N |
| R116 | R | CH₃OC(O)CH₂— | PhCH₂— | C |
| R117 | R | ClCH₂— | PhCH₂— | N |
| R118 | R | H₂NC(O)CH₂CH₂— | PhCH₂— | N |
| R119 | R | 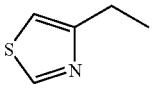 | PhCH₂— | N |
| R120 | R | 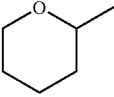 | PhCH₂— | N |
| R121 | R | CH₃— | CH₃OCH₂— | N |
| R122 | R | (CH₃)₂CH— | CH₃OCH₂— | C |
| R123 | R | PhCH₂— | CH₃OCH₂— | N |
| R124 | R | (CH3)₃C— | CH₃OCH₂— | N |
| R125 | R | PhCH₂OCH₂— | CH₃OCH₂— | C |
| R126 | R | CH₃— | [tetrahydropyran-2-yl] | N |
| R127 | R | CH₃— | Ph3C— | N |
| R128 | R | CH₃— | t-BuPh2Si— | N |
| R129 | R | CH₃— | t-BuMe2Si— | N |
| R130 | R | CH₃— | (CH₃)₃Si— | N |
| R131 | R | CH₃— | Et₃Si— | N |

TABLE 2

General formula (3)

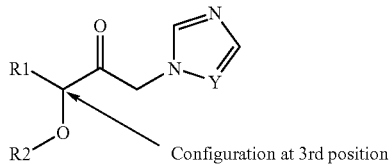

Configuration at 3rd position

| Compound number | Configuration at 3rd position | R1 | R2 | Y |
|---|---|---|---|---|
| S101 | S | CH₃— | CH₃— | N |
| S102 | S | (CH₃)₂CH— | CH₃— | N |
| S103 | S | PhCH₂— | CH₃— | N |
| S104 | S | (CH3)₃C— | CH₃— | C |
| S105 | S | PhCH₂OCH₂— | CH₃— | N |
| S106 | S | CH₃OC(O)CH₂— | CH₃— | N |
| S107 | S | ClCH₂— | CH₃— | N |
| S108 | S | H₂NC(O)CH₂CH₂— | CH₃— | C |
| S109 | S | 3-pyridyl-CH₂CH₂— | CH₃— | N |
| S110 | S | 4-thiazolyl-CH₂CH₂— | CH₃— | N |
| S111 | S | CH₃— | PhCH₂— | N |
| S112 | S | (CH₃)₂CH— | PhCH₂— | N |
| S113 | S | PhCH₂— | PhCH₂— | C |
| S114 | S | (CH3)₃C— | PhCH₂— | N |
| S115 | S | PhCH₂OCH₂— | PhCH₂— | N |
| S116 | S | CH₃OC(O)CH₂— | PhCH₂— | C |
| S117 | S | ClCH₂— | PhCH₂— | N |
| S118 | S | H₂NC(O)CH₂CH₂— | PhCH₂— | N |
| S119 | S | 3-pyridyl-CH₂CH₂— | PhCH₂— | N |
| S120 | S | 4-thiazolyl-CH₂CH₂— | PhCH₂— | N |
| S121 | S | CH₃— | CH₃OCH₂— | N |
| S122 | S | (CH₃)₂CH— | CH₃OCH₂— | C |
| S123 | S | PhCH₂— | CH₃OCH₂— | N |
| S124 | S | (CH3)₃C— | CH₃OCH₂— | N |
| S125 | S | PhCH₂OCH₂— | CH₃OCH₂— | C |
| S126 | S | CH₃— | 2-methyltetrahydropyranyl | N |
| S127 | S | CH₃— | Ph3C— | N |
| R128 | S | CH₃— | t-BuPh2Si— | N |
| R129 | S | CH₃— | t-BuMe2Si— | N |
| R130 | S | CH₃— | (CH₃)₃Si— | N |
| R131 | S | CH₃— | Et₃Si— | N |

TABLE 3
General formula (5)
| Compound number | Configuration 2nd | 3rd | R1 | R2 | 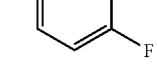 | Y |
|---|---|---|---|---|---|---|
| RR131 | R | R | PhCH$_2$— | CH$_3$— | 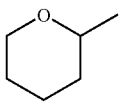 | C |
| RR132 | R | R | CH$_3$— | PhCH$_2$— | 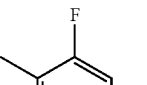 | N |
| RR133 | R | R | CH$_3$— | 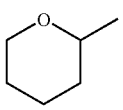 | 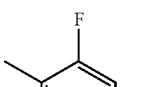 | N |
| RR134 | R | R | CH$_3$— | 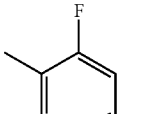 | 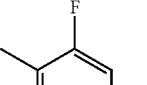 | C |
| RR135 | R | R | CH$_3$— | CH$_3$OCH$_2$— | 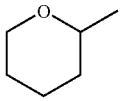 | N |
| RR136 | R | R | CH$_3$— | (CH$_3$)$_3$Si— | 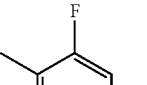 | N |
| RR137 | R | R | CH$_3$— |  |  | N |

TABLE 3-continued
General formula (5)
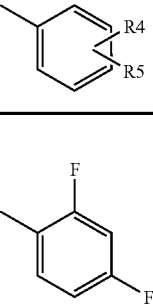
| Compound number | Configuration | | R1 | R2 | Aryl (R4,R5) | Y |
|---|---|---|---|---|---|---|
| | 2nd | 3rd | | | | |
| RR138 | R | R | CH$_3$— | Ph3C— | 2,4-F$_2$ | N |
| RR139 | R | R | CH$_3$— | t-BuPh2Si— | 2,4-F$_2$ | N |
| RR140 | R | R | CH$_3$— | PhCH$_2$— | 2,4-Cl$_2$ | N |
| RR141 | R | R | CH$_3$— | 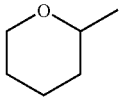 | 2,4-Cl$_2$ | N |
| RR142 | R | R | CH$_3$— | Et3Si— | 2,4-F$_2$ | N |
| RR143 | R | R | CH$_3$— | t-BuMe2Si- | 2,4-F$_2$ | N |

TABLE 3-continued
General formula (5)
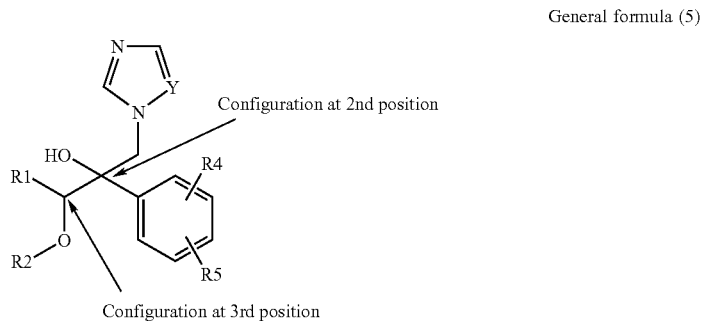
| Compound number | Configuration | | R1 | R2 | | Y |
|---|---|---|---|---|---|---|
| | 2nd | 3rd | | | | |
| RR144 | R | R | CH$_3$— | t-BuMe2Si- | 2,4-F$_2$C$_6$H$_3$ | C |
TABLE 4
General formula (5)
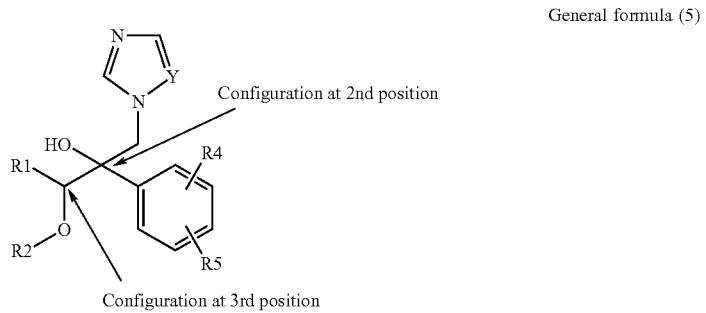
| Compound number | Configuration | | R1 | R2 | | Y |
|---|---|---|---|---|---|---|
| | 2nd | 3rd | | | | |
| SR131 | S | R | PhCH$_2$— | CH$_3$— | 2,4-F$_2$C$_6$H$_3$ | C |
| SR132 | S | R | CH$_3$— | PhCH$_2$— | 2,4-F$_2$C$_6$H$_3$ | N |

TABLE 4-continued

General formula (5)

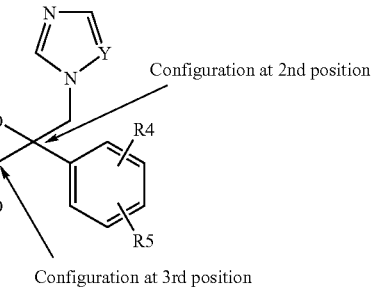

Configuration at 2nd position
Configuration at 3rd position

| Compound number | Configuration | | R1 | R2 | | Y |
|---|---|---|---|---|---|---|
| | 2nd | 3rd | | | R4/R5 | |
| SR133 | S | R | CH₃— | 2-tetrahydropyranyl | 2,4-diF-phenyl | N |
| SR134 | S | R | CH₃— | 2-tetrahydropyranyl | 2,4-diF-phenyl | C |
| SR135 | S | R | CH₃— | CH₃OCH₂— | 2,4-diF-phenyl | N |
| SR136 | S | R | CH₃— | (CH₃)₃Si— | 2,4-diF-phenyl | N |
| SR137 | S | R | CH₃— | 2-tetrahydropyranyl | 2,4-diF-phenyl | N |
| SR138 | S | R | CH₃— | Ph3C— | 2,4-diF-phenyl | N |
| SR139 | S | R | CH₃— | t-BuPh2Si— | 2,4-diF-phenyl | N |

TABLE 4-continued
General formula (5)
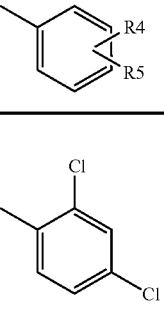
| Compound number | Configuration 2nd | Configuration 3rd | R1 | R2 | 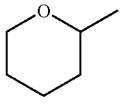 R4/R5 | Y |
|---|---|---|---|---|---|---|
| SR140 | S | R | CH₃— | PhCH₂— | 2,4-diCl-phenyl | N |
| SR141 | S | R | CH₃— | 2-tetrahydropyranyl | 2,4-diCl-phenyl | N |
TABLE 5
General formula (5)
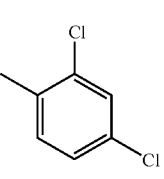
| Compound number | Configuration 2nd | Configuration 3rd | R1 | R2 | R4/R5 | Y |
|---|---|---|---|---|---|---|
| SS131 | S | S | PhCH₂— | CH₃— | 2,4-diF-phenyl | C |
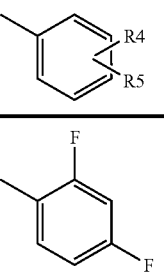

TABLE 5-continued
General formula (5)
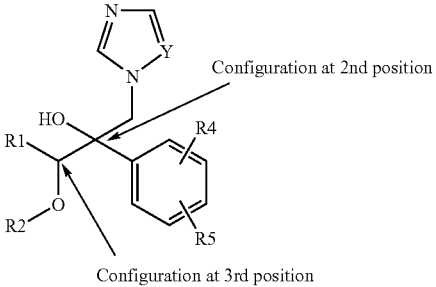
| Compound number | Configuration | | R1 | R2 |  | Y |
|---|---|---|---|---|---|---|
| | 2nd | 3rd | | | | |
| SS132 | S | S | CH₃— | PhCH₂— | 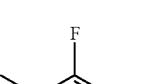 | N |
| SS133 | S | S | CH₃— | 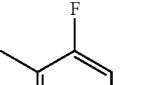 | 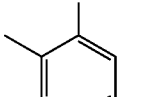 | N |
| SS134 | S | S | CH₃— | 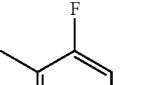 | 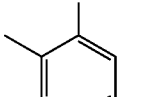 | C |
| SS135 | S | S | CH₃— | CH₃OCH₂— | 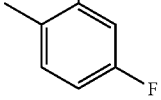 | N |
| SS136 | S | S | CH₃— | (CH₃)₃Si— | 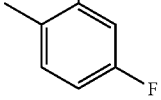 | N |
| SS137 | S | S | CH₃— | 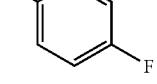 | 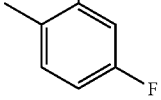 | N |

TABLE 5-continued
General formula (5)
Configuration at 2nd position
Configuration at 3rd position
| Compound number | Configuration | | R1 | R2 | 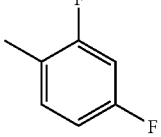 | Y |
|---|---|---|---|---|---|---|
| | 2nd | 3rd | | | | |
| SS138 | S | S | CH$_3$— | Ph3C— | 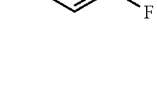 | N |
| SS139 | S | S | CH$_3$— | t-BuPh2Si— | 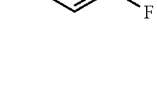 | N |
| SS140 | S | S | CH$_3$— | PhCH$_2$— | 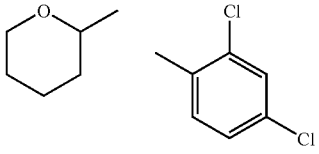 | N |
| SS141 | S | S | CH$_3$— |  | 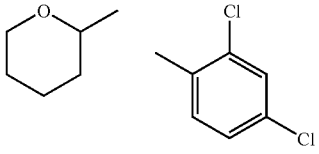 | N |

TABLE 6
General formula (5)
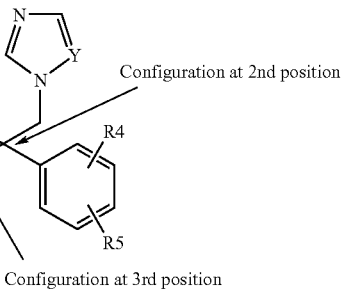
| Compound number | Configuration 2nd | 3rd | R1 | R2 | Ar (R4/R5) | Y |
|---|---|---|---|---|---|---|
| RS131 | R | S | PhCH₂— | CH₃— | 2,4-difluorophenyl | C |
| RS132 | R | S | CH₃— | PhCH₂— | 2,4-difluorophenyl | N |
| RS133 | R | S | CH₃— | tetrahydropyran-2-yl | 2,4-difluorophenyl | N |
| RS134 | R | S | CH₃— | tetrahydropyran-2-yl | 2,4-difluorophenyl | C |
| RS135 | R | S | CH₃— | CH₃OCH₂— | 2,4-difluorophenyl | N |
| RS136 | R | S | CH₃— | (CH₃)₃Si— | 2,4-difluorophenyl | N |
| RS137 | R | S | CH₃— | tetrahydropyran-2-yl | 2,4-difluorophenyl | N |

TABLE 6-continued
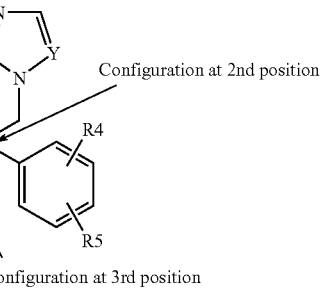
General formula (5)
| Compound number | Configuration | | R1 | R2 | Aryl (R4/R5) | Y |
|---|---|---|---|---|---|---|
| | 2nd | 3rd | | | | |
| RS138 | R | S | CH₃— | Ph3C— | 2,4-difluorophenyl | N |
| RS139 | R | S | CH₃— | t-BuPh2Si— | 2,4-difluorophenyl | N |
| RS140 | R | S | CH₃— | PhCH₂— | 2,4-dichlorophenyl | N |
| RS141 | R | R | CH₃— | 2-tetrahydropyranyl | 2,4-dichlorophenyl | N |

TABLE 7
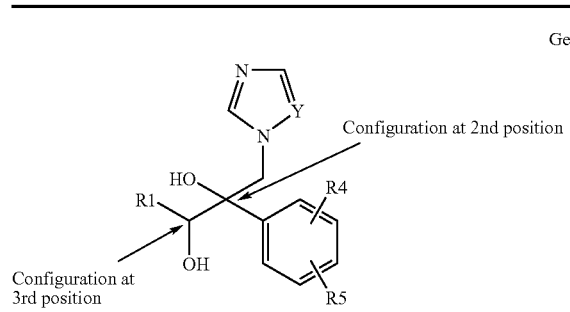
General formula (6)
| Compound number | Configuration | | R1 | 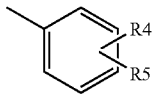 | Y |
|---|---|---|---|---|---|
| | 2nd | 3rd | | | |
| RR142 | R | R | CH$_3$— | 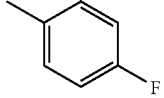 | C |
| RR143 | R | R | CH$_3$— | 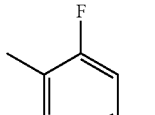 | N |
| RR144 | R | R | CH3CH2— | 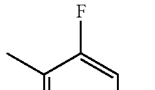 | N |
| RR145 | R | R | (CH$_3$)$_2$CH— | 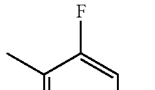 | C |
| RR146 | R | R | (CH$_3$)$_2$CH— | 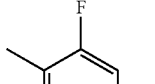 | N |
| RR147 | R | R | (CH$_3$)$_3$C— | 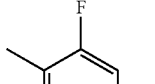 | N |

TABLE 7-continued

General formula (6)

| Compound number | Configuration | | R1 | R4/R5 | Y |
|---|---|---|---|---|---|
| | 2nd | 3rd | | | |
| RR148 | R | R | CH₃— | 4-F-phenyl | N |
| RR149 | R | R | CH₃— | 4-F-phenyl | C |
| RR150 | R | R | PhCH₂— | 2,4-F₂-phenyl | N |
| RR151 | R | R | CH₃— | 2,4-Cl₂-phenyl | N |
| RR152 | R | R | CH₃— | 2,4-Cl₂-phenyl | C |

TABLE 8
General formula (6)
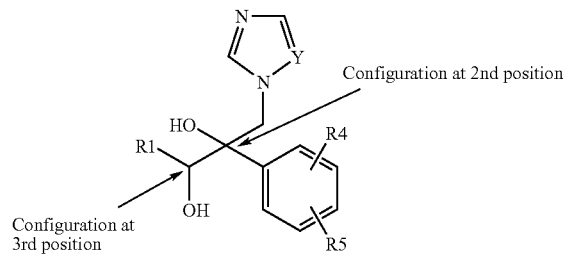
| Compound number | Configuration 2nd | 3rd | R1 | | Y |
|---|---|---|---|---|---|
| SR142 | S | R | CH₃— | 2,4-diF-phenyl | C |
| SR143 | S | R | CH₃— | 2,4-diF-phenyl | N |
| SR144 | S | R | CH3CH2— | 2,4-diF-phenyl | N |
| SR145 | S | R | (CH₃)₂CH— | 2,4-diF-phenyl | C |
| SR146 | S | R | (CH₃)₂CH— | 2,4-diF-phenyl | N |
| SR147 | S | R | (CH₃)₃C— | 2,4-diF-phenyl | N |
| SR148 | S | R | CH₃— | 4-F-phenyl | N |

TABLE 8-continued

General formula (6)

| Compound | Configuration | | | | |
|---|---|---|---|---|---|
| number | 2nd | 3rd | R1 | Ar (R4/R5) | Y |
| SR149 | S | R | CH₃— | 4-F-phenyl | C |
| SR150 | S | R | PhCH₂— | 2,4-F₂-phenyl | N |
| SR151 | S | R | CH₃— | 2,4-Cl₂-phenyl | N |
| SR152 | S | R | CH₃— | 2,4-Cl₂-phenyl | C |

TABLE 9
General formula (6)
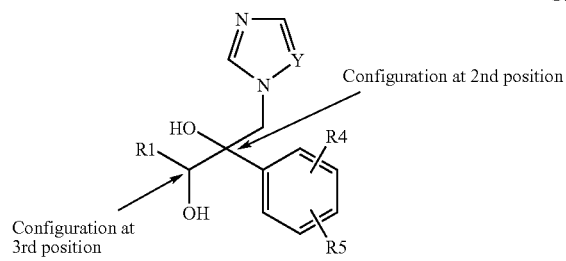
| Compound | Configuration | | | | |
|---|---|---|---|---|---|
| number | 2nd | 3rd | R1 | (aryl with R4, R5) | Y |
| SS142 | S | S | CH₃— | 2,4-difluorophenyl | C |
| SS143 | S | S | CH₃— | 2,4-difluorophenyl | N |
| SS144 | S | S | CH3CH2— | 2,4-difluorophenyl | N |
| SS145 | S | S | (CH₃)₂CH— | 2,4-difluorophenyl | C |
| SS146 | S | S | (CH₃)₂CH— | 2,4-difluorophenyl | N |
| SS147 | S | S | (CH₃)₃C— | 2,4-difluorophenyl | N |
| SS148 | S | S | CH₃— | 4-fluorophenyl | N |

TABLE 9-continued

General formula (6)

| Compound number | Configuration | | | | Y |
|---|---|---|---|---|---|
| | 2nd | 3rd | R1 | R4/R5 aryl | |
| SS149 | S | S | CH₃— | 4-F-phenyl | C |
| SS150 | S | S | PhCH₂— | 2,4-diF-phenyl | N |
| SS151 | S | S | CH₃— | 2,4-diCl-phenyl | N |
| SS152 | S | S | CH₃— | 2,4-diCl-phenyl | C |

TABLE 10
General formula (6)
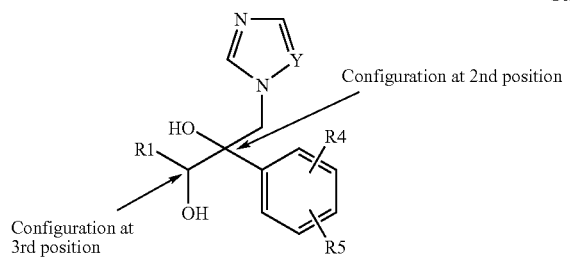
| Compound number | Configuration 2nd | 3rd | R1 | | Y |
|---|---|---|---|---|---|
| RS142 | R | S | CH₃— | 2,4-diF-phenyl | C |
| RS143 | R | S | CH₃— | 2,4-diF-phenyl | N |
| RS144 | R | S | CH3CH2— | 2,4-diF-phenyl | N |
| RS145 | R | S | (CH₃)₂CH— | 2,4-diF-phenyl | C |
| RS146 | R | S | (CH₃)₂CH— | 2,4-diF-phenyl | N |
| RS147 | R | S | (CH₃)₃C— | 2,4-diF-phenyl | N |
| RS148 | R | S | CH₃— | 4-F-phenyl | N |

TABLE 10-continued

General formula (6)

Configuration at 2nd position
Configuration at 3rd position

| Compound number | Configuration 2nd | Configuration 3rd | R1 | R4/R5 (aryl) | Y |
|---|---|---|---|---|---|
| RS149 | R | S | CH₃— | 4-F-phenyl | C |
| RS150 | R | S | PhCH₂— | 2,4-di-F-phenyl | N |
| RS151 | R | S | CH₃— | 2,4-di-Cl-phenyl | N |
| RS152 | R | S | CH₃— | 2,4-di-Cl-phenyl | C |

A typical method of the present invention will now be described.

[1] A method for producing an optically active azole-methyl ketone derivative represented by general formula (3) will now be described.

An azole-methyl ketone derivative represented by general formula (3) is produced by allowing an optically active α-alkoxycarboxylic acid derivative represented by general formula (1) to react with an azole acetic acid derivative represented by general formula (2) under a basic condition. According to this reaction, a decarboxylation proceeds after or during a carbon-carbon bonding reaction, thereby effectively introducing an azole methyl group. Although an optically active substance is used as the starting material, this reaction hardly decreases the optical purity of the resultant product.

The base used for the above reaction is not limited. Examples of the base include inorganic bases such as lithium hydroxide, sodium hydroxide, potassium hydroxide, sodium carbonate, potassium carbonate, and sodium hydrogencarbonate. Examples of the base include organic amine bases such as triethylamine, pyridine, and 1,8-diazabicycloundecene. Examples of the base include alkoxides such as sodium methoxide, sodium ethoxide, and potassium tert-butoxide. Examples of the base include metal hydrides such as lithium hydride and sodium hydride. Examples of the base include organometallic bases such as alkyl lithium and Grignard reagents, e.g., in particular, n-butyllithium, ethyl magnesium bromide, n-butyl magnesium chloride, and tert-butyl magnesium chloride. Examples of the base include metallic amide base such as sodium amide, lithium amide, and magnesium amide. In particular, examples of the metallic amide base include lithium diisopropylamide and magnesium halide dialkylamide, e.g., magnesium chloride diisopropylamide. These bases may be used alone or in combination of two or more.

Any solvent may be used as long as the reaction is not inhibited. Examples of the solvent include water; alcohols such as methanol, ethanol, and butanol; hydrocarbons such as hexane, toluene, and xylenes; esters such as ethyl acetate and butyl acetate; ethers such as diethyl ether, dioxane, ethylene glycol dimethyl ether, and tetrahydrofuran; halogenated hydrocarbons such as chloroform and dichloromethane; acetonitrile; dimethylformamide; dimethylsulfoxide; and dimethylimidazolidinone. These solvents may be used alone or in combination of two or more at any mixing ratio. The reaction temperature is generally in the range of −78° C. to the boiling point of the solvent used, and preferably, −20° C. to the boiling point of the solvent. Although the reaction time is not limited, the reaction time is generally in the range of several minutes to 24 hours, and preferably, 30 minutes to 6 hours.

[2] A method for producing an optically active azole-methyl alcohol derivative represented by general formula (5) will now be described.

An optically active azole-methyl alcohol derivative represented by general formula (5) is produced by allowing an optically active azole-methyl ketone derivative represented by general formula (3) to react with a phenyl metallic reagent represented by general formula (4). In this reaction, the diastereoselectivity depends on the combination of a protective group R2 for a hydroxyl group and a metal represented by A. Anti or syn configuration can be arbitrarily synthesized depending on the appropriate selection of the protective group and the metal.

In short, in this reaction, an organometallic reagent is allowed to react with the optically active azole-methyl ketone derivative according to a chelation model wherein the configuration of the oxygen atom in the R2O-group and the carbonyl group relating to the reaction is determined by the coordination of the metal. Thus, a desired product can be produced with high anti diastereoselectivity. In more detail, a compound having an S configuration selectively produces a compound having an S—R configuration, and a compound having an R configuration selectively produces a compound having an R—S configuration. In particular, for example, a benzyl or methoxymethyl group is used as the protective group and a Grignard reagent is used as the organometallic reagent. In this case, the desired reaction proceeds with high anti selectivity (>6:1).

On the other hand, a desired product can be produced with high syn selectivity by using a bulky protective group R2 for the hydroxyl group, and an appropriate metallic reagent. In more detail, a compound having an S configuration selectively produces a compound having an S—S configuration, and a compound having a R configuration selectively produces a compound having an R—R configuration with high syn selectivity (>4:1). The use of a silyl protective group allows the desired reaction to take place with significantly high syn selectivity (>20:1). Examples of the silyl protective group include trimethylsilyl, tert-butyldimethylsilyl, tert-butyldiphenylsilyl, and triethylsilyl groups.

Although an optically active substance is used as the starting material, this reaction hardly decreases the optical purity of the resultant product. Examples of a phenyl metallic compound include phenyl-lithium derivatives, phenyl-magnesium derivatives, phenyl-zinc derivatives, phenyl-titanium derivatives, phenyl-copper derivatives, and phenyl-copper-lithium derivatives. Additives may be added to the reaction system in order to change the diastereoselectivity and to improve the yield. Examples of the additives include Lewis acids and quaternary ammonium salts. In more detail, examples of the additives include $CeCl_3$, $MgBr_2$, $MgCl_2$, $ZnCl_2$, $ZnBr_2$, $CuCl_2$, $TiCl_4$, $BF_3$, $AlCl_3$, $SnCl_4$, and $SnCl_2$.

Any solvent may be used as long as the reaction is not inhibited. Examples of the solvent include water; alcohols such as methanol, ethanol, and butanol; hydrocarbons such as hexane, toluene, and xylenes; esters such as ethyl acetate and butyl acetate; ethers such as diethyl ether, dioxane, ethylene glycol dimethyl ether, and tetrahydrofuran; halogenated hydrocarbons such as chloroform and dichloromethane; acetonitrile; dimethylformamide; dimethylsulfoxide; and dimethylimidazolidinone. These solvents may be used alone or in combination of two or more at any mixing ratio. The reaction temperature is generally in the range of −78° C. to the boiling point of the solvent used, and preferably, −40° C. to room temperature. Although the reaction time is not limited, the reaction time is generally in the range of several minutes to 24 hours, and preferably, 30 minutes to 6 hours.

[3] A method for producing an optically active 2-phenyl-2,3-dihydroxypropyl azole derivative represented by general formula (6) will now be described.

An optically active 2-phenyl-2,3-dihydroxypropyl azole derivative represented by general formula (6) is produced by selectively deprotecting the protective group R2 for a hydroxyl group in an optically active azole-methyl alcohol derivative represented by general formula (5). The method for deprotecting the hydroxyl group is not limited as long as the molecular structure other than the deprotected portion is not changed. An ether protective group is deprotected by acid treatment using, for example, hydrochloric acid, sulfuric acid, trifluoroacetic acid, p-toluene sulfonic acid, or acetic acid; or by catalytic hydrogenation using a catalyst such as palladium-carbon. An acetal protective group is deprotected by acid treatment using, for example, hydrochloric acid, sulfuric acid, trifluoroacetic acid, p-toluene sulfonic acid, pyridinium p-toluene sulfonic acid, or acetic acid. A silyl protective group is deprotected by acid treatment using, for example, hydrochloric acid, sulfuric acid, trifluoroacetic acid, p-toluene sulfonic acid, pyridinium p-toluene sulfonic acid, or acetic acid; or by fluoride anion treatment using, for example, tetra-n-butyl-ammonium fluoride. Any solvent may be used as long as the reaction is not inhibited. Examples of the solvent include water; alcohols such as methanol, ethanol, and butanol; hydrocarbons such as hexane, toluene, and xylenes; esters such as ethyl acetate and butyl acetate; ethers such as diethyl ether, dioxane, ethylene glycol dimethyl ether, and tetrahydrofuran; halogenated hydrocarbons such as chloroform and dichloromethane; acetonitrile; dimethylformamide; and dimethylsulfoxide. These solvents may be used alone or in combination of two or more at any mixing ratio. The reaction temperature is generally in the range of −20° C. to the boiling point of the solvent used. Although the reaction time is not limited, the reaction time is generally in the range of several minutes to 24 hours, and preferably, 30 minutes to 6 hours.

The optically active α-hydroxycarboxylic acid derivative represented by general formula (1) is readily and commercially available or can be synthesized by generally known methods. For example, the optically active α-hydroxycarboxylic acid derivative can be synthesized by using lactic acid (Chem. Pharm. Bull., Vol. 41 (6), PP. 1035-1042, 1993), various amino acids (Synthesis, 1987, P. 479), or an α-halocarboxylic acid derivative (Tetrahedron Lett., 1985, Vol. 26, P. 5257). The azole acetic acid derivative represented by general formula (2) can be readily synthesized by known methods (for example, Tetrahedron Lett., 2000, 41 (8), 1297). In the present invention, methods for producing some reagents and starting materials are not specifically described. In general, these reagents and materials are commercially available, and therefore readily available.

Although examples of the present invention will now be described, the present invention is not limited to the following examples.

EXAMPLE 1

Synthesis of (3R)-1-(1H-1,2,4-triazol-1-yl)-3-(triphenylmethyloxy)-2-butanone

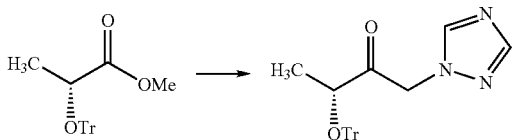

Tetrahydrofuran (4 mL) and triethylamine (0.44 g) were added to triazole acetic acid (0.55 g) and the mixture was stirred at room temperature for two hours. Subsequently, methyl (2R)-2-(triphenylmethyloxy) propionate (1.00 g) was mixed with the mixture at room temperature. The resultant homogeneous mixture is hereinafter referred to as Solution A. A solution (25 mL) of tetrahydrofuran containing tert-butyl magnesium chloride (0.91 M) was heated at 40° C. to 45° C. Solution A was added dropwise to the solution for one hour. The mixture was then stirred at 40° C. to 45° C. for four hours. The reaction mixture was cooled on ice to 50° C., and sulfuric acid (2 N, 30 mL) was added dropwise to the mixture. Ethyl acetate (50 mL) was added to the mixture to extract the target compound. Thus, an organic layer was separated. The organic layer was washed with saturated sodium bicarbonate (40 mL), and subsequently washed with a saturated saline solution (40 mL). The washed organic layer was dried with anhydrous sodium sulfate, and was then concentrated. The resultant substance was purified by silica gel column chromatography (equivalent to Merck C-300, 15 g, pure chloroform to chloroform:methanol=8:2). The resultant substance was crystallized with hexane to recover light yellow crystals of the target compound (0.60 g, 52%).

Melting point: 162° C. (decomposition) $^1$H-N.M.R. (270 MHz, CDCl$_3$): δ=7.84(s, 1H), 7.48(s, 1H), 7.45-7.25(m, 15H), 5.01(d, 1H, J=8.8 Hz), 4.40(q, 1H, J=6.9 HZ), 4.07(d, 1H, J=8.8 Hz), and 1.51(d, 3H, J=6.9 Hz)

EXAMPLE 2

Synthesis of (3R)-3-(benzyloxy)-1-(1H-1,2,4-triazol-1-yl)-2-butanone

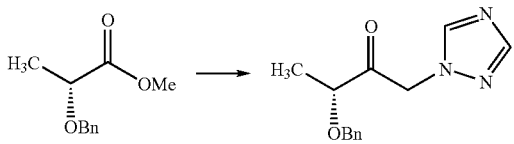

The target compound (7.6 g, 30%), which was a transparent and colorless syrup, was recovered as in Example 1, except methyl (2R)-2-(benzyloxy) propionate (20.0 g) was used instead of methyl (2R)-2-(triphenylmethyloxy) propionate.

$^1$H-N.M.R. (270 MHz, DMSO-d6): δ=8.44(s, 1H), 7.98(s, 1H), 7.50-7.20(m, 5H), 5.55(d, 1H, J=18.6 Hz), 5.43(d, 1H, J=18.6 Hz), 4.61(s, 2H), 4.26(q, 1H, J=6.9 Hz), and 1.34(d, 3H, J=6.9 Hz)

EXAMPLE 3

Synthesis of (3S)-3-(benzyloxy)-1-(1H-1,2,4-triazol-1-yl)-2-butanone

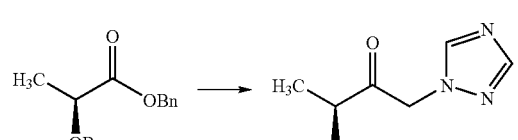

The target compound (340 mg, 19%), which was a transparent and colorless syrup, was recovered as in Example 1, except benzyl (2S)-2-(benzyloxy) propionate (1.88 g) was used instead of methyl (2R)-2-(triphenylmethyloxy) propionate. The values of the physical properties corresponded with those in Example 2.

EXAMPLE 4

Synthesis of (3R)-3-(methoxymethyloxy)-1-(1H-1,2,4-triazol-1-yl)-2-butanone

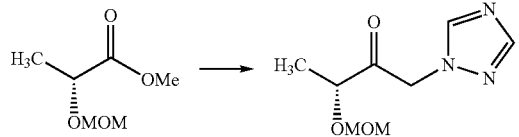

The target compound (1.59 g, 40%), which was a transparent and colorless syrup, was recovered as in Example 1, except methyl (2R)-2-(methoxymethyloxy) propionate (2.96 g, 20 mmol) was used instead of methyl (2R)-2-(triphenylmethyloxy) propionate.

$^1$H-N.M.R. (270 MHz, CDCl$_3$) : δ=8.14 (s, 1H), 7.97(s, 1H), 5.36(d, 1H, J=8.8 Hz), 5.22(d, 1H, J=8.8 Hz), 4.73-4.70(m, 1H), 4.40(q, 1H, J=6.9 Hz), 3.95-3.87(m, 1H), 3.59-3.52(m, 1H), 1.91-1.55(m, 6H), and 1.48(d, 3H, J=6.9 Hz)

EXAMPLE 5

Synthesis of (3R)-3-(tert-butyldimethylsilyloxy)-1-(1H-1,2,4-triazol-1-yl)-2-butanone

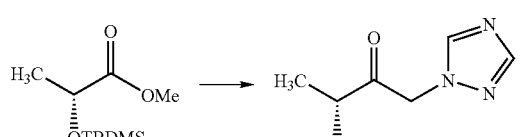

Tetrahydrofuran (15 mL) was added to triazole sodium acetate (1.02 g, 6.87 mmol) and anhydrous magnesium chloride (1.31 g, 13.7 mmol), and the mixture was stirred at room temperature for two hours. A solution (15.1 mL) of tetrahydrofuran containing tert-butyl magnesium chloride (0.91 M) was added to the mixture, and the mixture was heated at 40° C. to 45° C. Subsequently, a solution of tetrahydrofuran (3 mL) containing methyl (2R)-2-(tert-butyldimethylsilyloxy)propionate (1.00 g 4.58 mmol) was added dropwise to the mixture at 40° C. to 45° C. for one hour. The mixture was then stirred at 40° C. to 45° C. for four hours. Sulfuric acid (10%) was added to the reaction mixture so that the pH of the reaction mixture was controlled in the range of 2 to 4. The target compound was extracted with toluene (20 mL). The extracted solution was washed with water, and was then dried with anhydrous magnesium sulfate. The drying agent was filtered, and the filtrate was concentrated under reduced pressure. The resultant crude product was purified by silica gel column chromatography (equivalent to Merck C-300, 15 g, hexane:ethyl acetate=3:1 to 2:1 to 1:1) to recover the target compound (1.09 g, 82%), which was a transparent and colorless syrup.

$^{1}$H-N.M.R. (270 MHz, CDCl$_{3}$): δ=8.14(s, 1H), 7.98(s, 1H), 5.42(d, 1H, J=19.1 Hz), 5.22(d, 1H, J=19.1 Hz), 4.39(q, 1H, J=6.9 Hz), 1.40(d, 3H, J=6.9 Hz), 0.97(s, 9H), and 0.16(s, 6H)

Optical purity by a chiral HPLC area method: 99% ee
Analytical conditions/DAICEL CHIRALPAK AD, Eluent composition: hexane:2-propanol:diethylamine=90:10: 0.1, Detection method: UV 220 nm

EXAMPLE 6

Synthesis of (3R)-3-(3,4,5,6-tetrahydro-2H-pyran-1-yloxy)-1-(1H-1,2,4-triazol-1-yl)-2-butanone

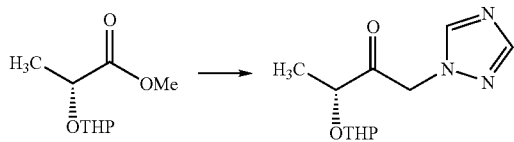

The target compound (2.15 g, 45%), which was a transparent and colorless syrup and was a mixture of two diastereomers derived from the THP group, was recovered as in Example 1, except methyl (2R)-2-(3,4,5,6-tetrahydro-2H-pyran-1-yloxy) propionate (3.77 g, 20 mmol) was used.

THP group-derived diastereomer A; $^{1}$H-N.M.R. (270 MHz, CDCl$_{3}$): δ=8.11(s, 1H), 7.97(s, 1H), 5.36(d, 1H, J=8.8 Hz), 5.22(d, 1H, J=8.8 Hz), 4.73-4.70(m, 1H), 4.40(q, 1H, J=6.9 Hz), 3.95-3.87(m, 1H), 3.59-3.52(m, 1H), 1.91-1.55 (m, 6H), and 1.48(d, 3H, J=6.9 Hz)

THP group-derived diastereomer B; $^{1}$H-N.M.R. (270 MHz, CDCl$_{3}$): δ=8.11(s, 1H), 7.96(s, 1H), 5.50(d, 1H, J=8.8 Hz), 5.32(d, 1H, J=8.8 Hz), 4.57-4.54(m, 1H), 4.24(q, 1H, J=6.9 Hz), 3.95-3.89(m, 1H), 3.52-3.42(m, 1H), 1.89-1.84 (m, 2H), 1.57-1.54(m, 4H), and 1.39(d, 3H, J=6.9 Hz)

EXAMPLE 7

Synthesis of (2R, 3R)-2-(2,4-difluorophenyl)-3-(methoxymethyloxy)-1-(1H-1,2,4-triazol-1-yl)-2-butanol and (2S, 3R)-2-(2,4-difluorophenyl)-3-(methoxymethyloxy)-1-(1H-1,2,4-triazol-1-yl)-2-butanol

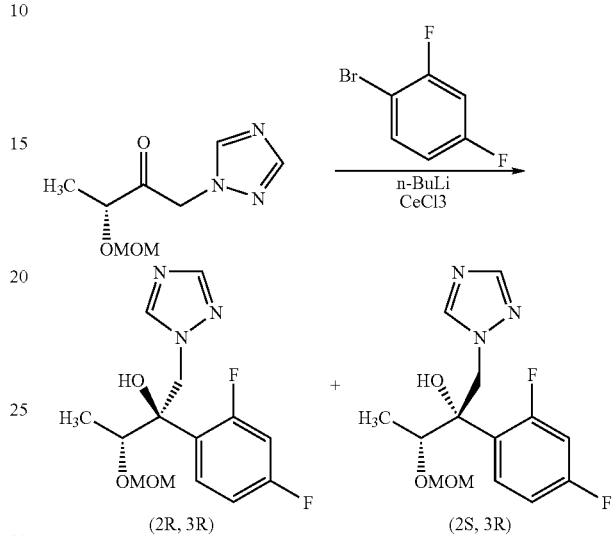

2,4-Difluorobromobenzene (202 mg, 1.05 mmol) was dissolved in ether (4 mL). A solution of hexane (0.66 mL, 1.05 mmol) containing n-butyllithium (1.59 M) was added dropwise to the mixture at −70° C. to −65° C., and the mixture was stirred for 30 minutes. The resultant mixture is hereinafter referred to as Mixture A. Anhydrous cerium chloride (258 mg, 1.05 mmol) was dried at 140° C. for one hour under reduced pressure, and was then cooled to room temperature. Tetrahydrofuran (3 mL) was added to the anhydrous cerium chloride, and was subsequently subjected to ultrasonic treatment for 30 minutes. The resultant suspension is hereinafter referred to as Suspension B. Suspension B was added dropwise to Mixture A, which was cooled at a temperature in the range of −70° C. to −65° C. Subsequently, a solution of ether (2 mL) containing (3R)-3-(methoxymethyloxy)-1-(1H-1,2,4-triazol-1-yl)-2-butanone (70 mg, 0.35 mmol) was added dropwise to the mixture at −70° C. to −65° C. The mixture was stirred at this temperature for 30 minutes. The temperature of the mixture was then increased to room temperature. Ethyl acetate (10 mL) and water (10 mL) were added to the reaction mixture and an organic layer was separated. The organic layer was washed with a saturated saline solution (5 mL) and was then dried with anhydrous magnesium sulfate. The drying agent was filtered and the filtrate was concentrated under reduced pressure. The resultant product was purified by preparative silica gel thin layer chromatography (Merck, 20 cm×20 cm×2 mm, developing solution: pure ethyl acetate) to recover the target compound (38 mg, 35%), which was a mixture of diastereomers. The compound was a transparent and colorless syrup. The ratio of the diastereomers was (2R, 3R):(2S, 3R)=6:1. The ratio of the diastereomers was determined by derivatives, as will be described in Example 18, in which the methoxymethyl group was deprotected.

(2R, 3R)-Diastereomer; $^{1}$H-N.M.R. (270 MHz, CDCl$_{3}$): δ=7.89(s, 1H), 7.73(s, 1H), 7.48-7.38(m, 1H), 6.79-6.71(m, 2H), 4.91-4.72(m, 4H), 4.29(q, 1H, J=6.6 Hz), 4.13(s, 1H), 3.46(s, 3H), and 1.03(d, 3H, J=6.6 Hz)

(2S, 3R)-Diastereomer; $^1$H-N.M.R. (270 MHz, CDCl$_3$): δ=8.02(s, 1H), 7.72(s, 1H), 7.49-7.40(m, 1H), 6.79-6.69(m, 2H), 4.99(d, 1H, J=13.8 Hz), 4.59(d, 1H, J=7.0 Hz), 4.48(d, 1H, J=13.8 Hz), 4.42(d, 1H, J=7.0 Hz), 4.41(s, 1H), 4.15(q, 1H, J=6.3 Hz), 3.08(s, 3H), and 1.28(d, 3H, J=6.3 Hz)

EXAMPLE 8

Synthesis of (2R, 3R)-3-(benzyloxy)-2-(2,4-difluorophenyl)-1-(1H-1,2,4-triazol-1-yl)-2-butanol and (2S, 3R)-3-(benzyloxy)-2-(2,4-difluorophenyl)-1-(1H-1,2,4-triazol-1-yl)-2-butanol

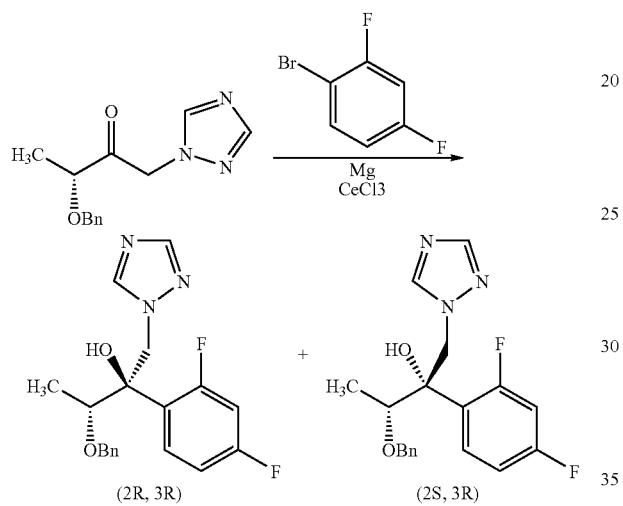

Magnesium (6.0 g, 46 mmol) was dispersed in tetrahydrofuran. (120 mL) in a nitrogen atmosphere. Iodine (5 mg) was-added and the mixture was stirred. A solution of tetrahydrofuran (120 mL) containing 2,4-difluorobromobenzene (48 g, 248 mmol) was added dropwise to the mixture so that the internal temperature was controlled 30° C. to 35° C. The resultant mixture is hereinafter referred to as Grignard reagent A. Anhydrous cerium chloride (10 g, 40.8 mmol) was dried at 130° C. for one hour under reduced pressure, and was then cooled to room temperature. Tetrahydrofuran (40 mL) was added to the anhydrous cerium chloride in a nitrogen atmosphere, and the resultant suspension was subsequently subjected to ultrasonic treatment for 30 minutes. The suspension is hereinafter referred to as Suspension B. Subsequently, a solution of tetrahydrofuran (10 mL) containing (3R)-3-(benzyloxy)-1-(1H-1,2,4-triazol-1-yl)-2-butanone (5.0 mg, 20.4 mmol) was added to Suspension B, and the mixture was further subjected to ultrasonic treatment for 30 minutes. Tetrahydrofuran (4 mL) was added to the resultant Suspension B, and then the temperature of the suspension was kept at 0° C. to −5° C. Grignard reagent A (24 mL, 24 mmol) was added dropwise to the suspension. Subsequently, the mixture was further stirred for 12 hours. The reaction mixture was cooled on ice and hydrochloric acid (1 N, 200 mL) was added dropwise to the mixture. Ethyl acetate (400 mL) was added to the mixture to extract the target compound. Thus, an organic layer was separated. The organic layer was washed with a saturated aqueous solution of sodium hydrogencarbonate (400 mL), and subsequently washed with a saturated saline solution (400 mL). The organic layer was then dried with magnesium sulfate. The drying agent was filtered and the filtrate was concentrated to produce an oily product (10 g). The product was purified by silica gel column chromatography (equivalent to Merck C-300, 10 g, hexane:ethyl acetate=2:1 to 1:1) to recover the target compound (900 mg, 12%). The compound was a transparent and colorless syrup. The ratio of the diastereomers was (2R, 3R):(2S, 3R)=1:14. The ratio of the diastereomers was determined by derivatives, as will be described in Example 14, in which the benzyl group was deprotected.

(2R, 3R)-Diastereomer; $^1$H-N.M.R. (400 MHz, CDCl$_3$): δ=7.85(s, 1H), 7.67(s, 1H), 7.42-7.30(m, 6H), 6.76-6.68(m, 2H), 4.77(d, 1H, J=11.5 Hz), 4.72(s, 2H), 4.51(d, 1H, J=11.5 Hz), 4.15(q, 1H, J=6.3 Hz), 4.02(s, 1H), and 1.04(d, 1H, J=6.3 Hz)

(2S, 3R)-Diastereomer; $^1$H-N.M.R. (400 MHz, CDCl$_3$): δ=7.99(s, 1H), 7.72(s, 1H), 7.49-7.43(m, 1H), 7.29-7.26(m, 3H), 7.10-7.08(m, 2H), 6.80-6.75(m, 1H), 6.71-6.65(m, 1H), 4.96(d, 1H, J=14.5 Hz), 4.53(d, 1H, J=10.4 Hz), 4.45(d, 1H, J=14.5 Hz), 4.36(s, 1H), 4.27(d, 1H, J=10.4 Hz), 3.90(q, 1H, J=6.1 Hz), and 1.25(d, 3H, J=6.1 Hz)

The above mixture of diastereomers, which was a transparent and colorless syrup, was crystallized by using hexane and ethyl acetate as the crystallization solvent. White crystals (40 g, 10%) of the (2R, 3S)-diastereomer were preferentially recovered. Melting point: 103° C. to 105° C., Diastereomeric excess: 98% de The diastereomeric excess was determined by derivatives, as will be described in Example 14, in which the benzyl group was deprotected.

EXAMPLE 9

Synthesis of (2S, 3S)-2-(2,4-difluorophenyl)-3-(methoxymethyloxy)-1-(1H-1,2,4-triazol-1-yl)-2-butanol and (2R, 3S)-2-(2,4-difluorophenyl)-3-(methoxymethyloxy)-1-(1H-1,2,4-triazol-1-yl)-2-butanol

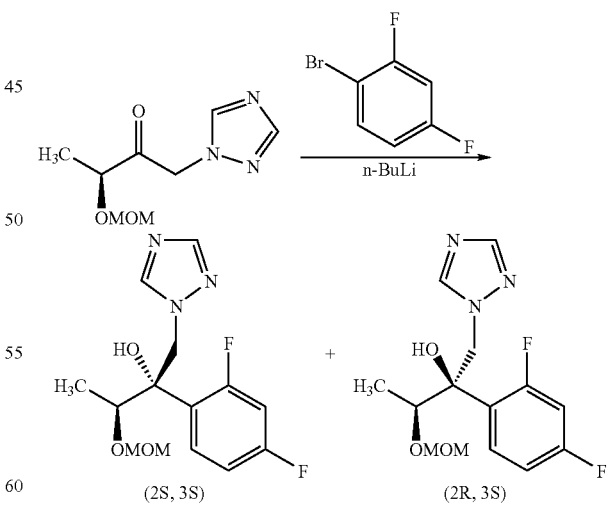

2,4-Difluorobromobenzene (139 mg, 0.72 mmol) was dissolved in tetrahydrofuran (4 mL). A solution of hexane (0.45 mL, 0.72 mmol) containing n-butyllithium (1.59 M) was added dropwise to the mixture at −70° C. to −65° C., and the mixture was stirred for 30 minutes. Subsequently, a solution of ether (1 mL) containing (3S)-3-(methoxymethyloxy)-1-(1H-1,2,4-triazol-1-yl)-2-butanone (47.5 mg, 0.24 mmol) was added dropwise to the mixture at −70° C. to −65° C. The mixture was stirred at this temperature for 30 minutes. The temperature of the mixture was then increased to room temperature. Ethyl acetate (10 mL) and water (10 mL) were added to the reaction mixture and an organic layer was separated. The organic layer was washed with a saturated saline solution (5 mL) and was then dried with anhydrous magnesium sulfate. The drying agent was filtered and the filtrate was concentrated under reduced pressure. The resultant product was purified by preparative silica gel thin layer chromatography (Merck, 20 cm×20 cm×2 mm, developing solution: pure ethyl acetate) to recover the target compound (15 mg, 20%), which was a mixture of diastereomers. The compound was a transparent and colorless syrup. The ratio of the diastereomers was (2S, 3S):(2R, 3S)=5:1. The ratio of the diastereomers was determined by derivatives, as will be described in Example 18, in which the methoxymethyl group was deprotected. The values of the physical properties corresponded with those in Example 7.

EXAMPLE 10

Synthesis of (2R, 3R)-2-(2,4-difluorophenyl)-1-(1H-1,2,4-triazol-1-yl)-3-(triphenylmethyloxy)-2-butanol and (2S, 3R)-2-(2,4-difluorophenyl)-1-(1H-1,2,4-triazol-1-yl)-3-(triphenylmethyloxy)-2-butanol

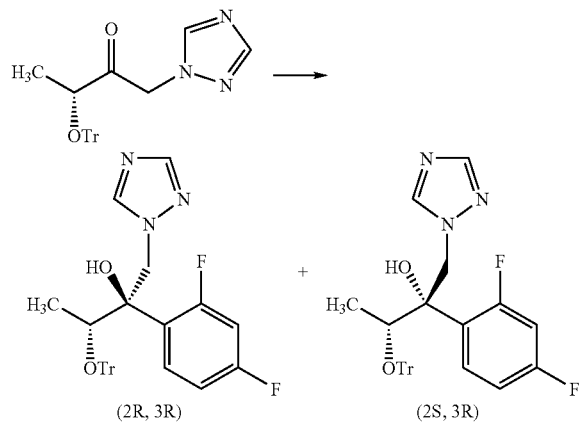

The target compound (200 mg, 10%), which was a mixture of diastereomers, was recovered as in Example 7, except (3R)-1-(1H-1,2,4-triazol-1-yl)-3-(triphenylmethyloxy)-2-butanone (1.55 g) was used instead of (3R)-3-(methoxymethyloxy)-1-(1H-1,2,4-triazol-1-yl)-2-butanone. The target compound was a light yellow syrup. The ratio of the diastereomers was (2R, 3R):(2S, 3R)=4.3:1. The ratio of the diastereomers was determined by derivatives, as will be described in Example 17, in which the trityl group was deprotected.

(2R, 3R)-Diastereomer; $^1$H-N.M.R. (270 MHz, CDCl$_3$): δ=8.10-7.08(m, 18H), 6.79-6.49(m, 2H), 4.47(d, 1H, J=15 Hz), 4.40-4.20(m, 2H), 3.79(q, 1H, J=6.9 Hz), and 0.80(d, 3H, J=6.9 Hz)

(2S, 3R)-Diastereomer; $^1$H-N.M.R. (270 MHz, CDCl$_3$): δ=8.10-7.08(m, 18H), 6.79-6.49(m, 2H), 4.58(d, 1H, J=15 Hz), 4.46(s, 1H), 4.30-4.20(m, 1H), 3.71(q, 1H, J=6.9 Hz), and 1.00(d, 3H, J=6.9 Hz)

EXAMPLE 11

Synthesis of (2R, 3R)-2-(2,4-difluorophenyl)-3-(methoxymethyloxy)-1-(1H-1,2,4-triazol-1-yl)-2-butanol and (2S, 3R)-2-(2,4-difluorophenyl)-3-(methoxymethyloxy)-1-(1H-1,2,4-triazol-1-yl)-2-butanol

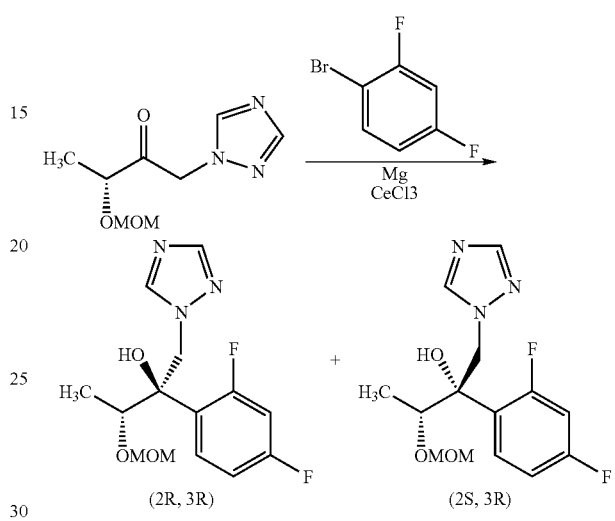

The target compound (28 mg, 37%), which was a mixture of diastereomers, was recovered as in Example 8, except (3R)-3-(methoxymethyloxy)-1-(1H-1,2,4-triazol-1-yl)-2-butanone (48 mg, 0.35 mmol) was used instead of (3R)-3-(benzyloxy)-1-(1H-1,2,4-triazol-1-yl)-2-butanone. The target compound was a transparent and colorless syrup. The ratio of the diastereomers was (2R, 3R):(2S, 3R)=1:8. The ratio of the diastereomers was determined by derivatives, as will be described in Example 18, in which the methoxymethyl group was deprotected. The values of the physical properties corresponded with those in Example 9.

EXAMPLE 12

Synthesis of (2R, 3R)-3-(tert-butyldimethylsilyloxy)-2-(2,4-difluorophenyl)-1-(1H-1,2,4-triazol-1-yl)-2-butanol and (2S, 3R)-3-(tert-butyldimethylsilyloxy)-2-(2,4-difluorophenyl)-1-(1H-1,2,4-triazol-1-yl)-2-butanol

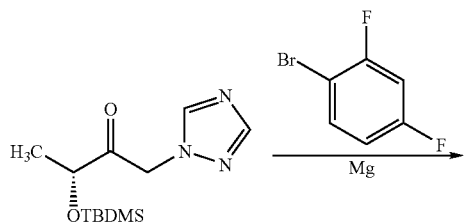

-continued

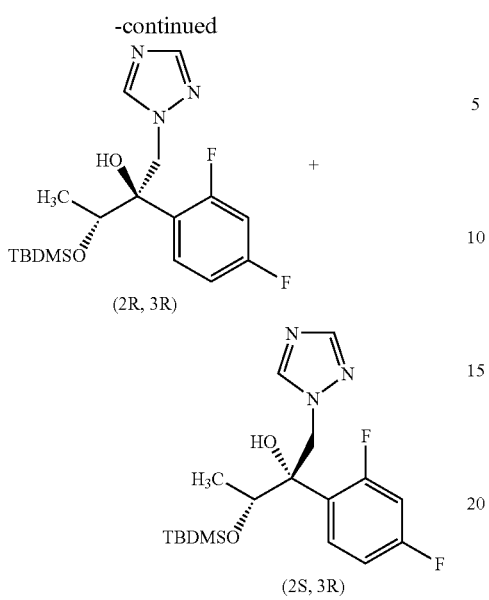

(2R, 3R)

(2S, 3R)

Magnesium (5.96 g, 245 mmol) was dispersed in tetrahydrofuran (175 g), and iodine (5 mg) was added to the dispersion liquid. A solution of tetrahydrofuran (60 g) containing 2,4-difluorobromobenzene (47.3 g, 245 mmol) was added dropwise to the mixture at room temperature to prepare a Grignard reagent. (3R)-3-(Tert-butyldimethylsilyloxy)-1-(1H-1,2,4-triazol-1-yl)-2-butanone (20 g, 74.2 mmol) and anhydrous magnesium chloride (21.2 g, 223 mmol) were suspended in tetrahydrofuran (100 g), and the suspension was cooled to −35° C. The above Grignard reagent was added dropwise to the suspension for 45 minutes. Subsequently, the suspension was stirred for 15 minutes and then hydrochloric acid (1 N, 245 mL) was added to stop the reaction. Toluene (180 mL) was added to the mixture to extract the target compound. Thus, an organic layer was separated. The organic layer was washed with water (90 mL). The organic layer was then dried with anhydrous magnesium sulfate. The drying agent was filtered and the filtrate was concentrated under reduced pressure. The product was purified by silica gel column chromatography (equivalent to Merck C-300, 300 g, hexane:ethyl acetate=3:1 to 3:2 to 1:1) to recover the target compound (21.9 g, 77%), which was a mixture of diastereomers. The compound was a light yellow syrup. The ratio of the diastereomers was (2R, 3R):(2S, 3R)=23:1. The ratio of the diastereomers was determined by derivatives, as will be described in Example 15, in which the tert-butyldimethylsilyl group was deprotected.

(2R, 3R)-Diastereomer; $^1$H-N.M.R. (270 MHz, CDCl$_3$): δ=7.94(s, 1H), 7.68(s, 1H), 7.42-7.33(m, 1H), 6.80-6.71(m, 2H), 4.82(d, 1H, J=13.8 Hz), 4.55(d, 1H, J=13.8 Hz), 4.45-4.42(m, 1H), 3.77(s, 1H), 0.98(d, 3H, J=6.0 Hz), 0.98 (s, 9H), and 0.18(s, 6H)

(2S, 3R)-Diastereomer; $^1$H-N.M.R. (270 MHz, CDCl$_3$): δ=8.17(s, 1H), 7.80(s, 1H), 7.42-7.33(m, 1H), 6.80-6.71(m, 2H), 4.96(d, 1H, J=13.8 Hz), 4.57(d, 1H, J=13.8 Hz), 4.35-4.25(m, 1H), 3.77(s, 1H), 1.22(d, 3H, J=6.0 Hz), 0.90 (s, 9H), and 0.09(s, 6H)

The above mixture of diastereomers, which was a light yellow syrup, was crystallized by using hexane as the crystallization solvent. White crystals (17.3 g, 61%) of the (2R, 3R)-diastereomer were preferentially recovered. Melting point: 106° C. to 107° C., Diastereomeric excess: 99.5% de The diastereomeric excess was determined by derivatives, as will be described in Example 15, in which the tert-butyldimethylsilyl group was deprotected. Optical purity by a chiral HPLC area method: 99% ee Analytical conditions/DAICEL CHIRALPAK AD, Eluent composition: hexane:2-propanol:diethylamine=90:10:0.1, Detection method: UV 254 nm

EXAMPLE 13

Synthesis of (2R, 3R)-3-(tert-butyldimethylsilyloxy)-2-(2,4-difluorophenyl)-1-(1H-1,2,4-triazol-1-yl)-2-butanol and (2S, 3R)-3-(tert-butyldimethylsilyloxy)-2-(2,4-difluorophenyl)-1-(1H-1,2,4-triazol-1-yl)-2-butanol

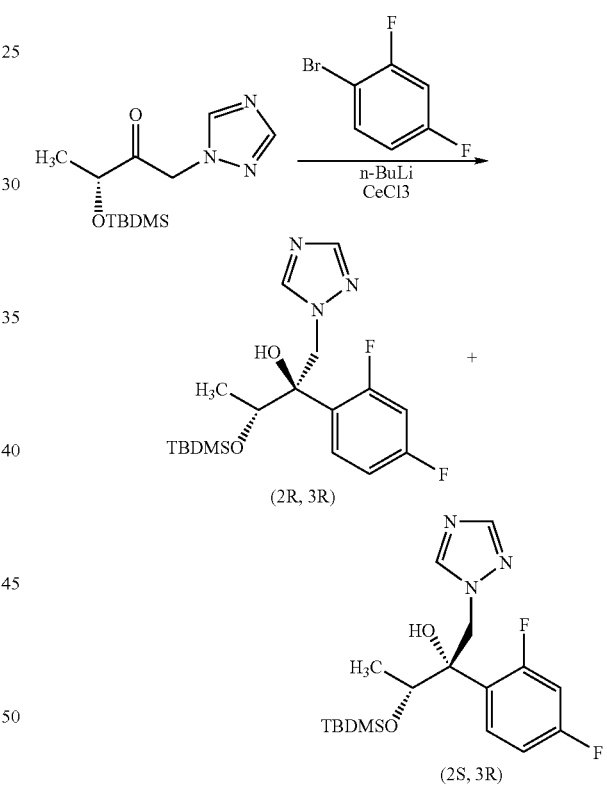

(2R, 3R)

(2S, 3R)

The target compound (36 mg, 46%), which was a mixture of diastereomers, was recovered as in Example 7, except (3R)-3-(tert-butyldimethylsilyloxy)-1-(1H-1,2,4-triazol-1-yl)-2-butanone (55 mg, 0.204 mmol) was used instead of (3R)-3-(methoxymethyloxy)-1-(1H-1,2,4-triazol-1-yl)-2-butanone. The target compound was a light yellow syrup. The ratio of the diastereomers was (2R, 3R):(2S, 3R)=6:1.

The ratio of the diastereomers was determined by derivatives, as will be described in Example 15, in which the tert-butyldimethylsilyl group was deprotected. The values of the physical properties corresponded with those in Example 12.

EXAMPLE 14

Synthesis of (2S, 3R)-2-(2,4-difluorophenyl)-1-(1H-1,2,4-triazol-1-yl)-2,3-butanediol

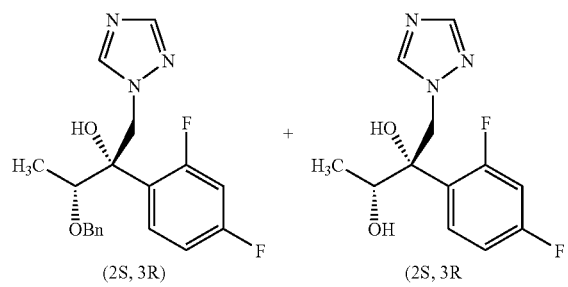

(2S, 3R)             (2S, 3R)

The (2S, 3R)-3-(benzyloxy)-2-(2,4-difluorophenyl)-1-(1H-1,2,4-triazol-1-yl)-2-butanol (719 g, 2 mmol) synthesized in Example 8 was dissolved in methanol (30 mL). Fifty percent-hydrated 10%-palladium-carbon (0.3 g) was added to the solution and the mixture was stirred in an autoclave at 1.0 MPa of hydrogen initial pressure, at 50° C. for eight hours. The catalyst was filtered from the reaction solution and the filtrate was concentrated under reduced pressure to recover the target compound (480 mg, 89%). The compound was a white amorphous solid. Diastereomeric excess: 98% de Analytical conditions/YMC-PACK ODS A-303, Eluent composition: methanol:water:acetic acid=70:30:0.2, Detection method: UV 254 nm $^1$H-N.M.R. (270 MHz, CDCl$_3$): δ=8.04(s, 1H), 7.77(s, 1H), 7.58-7.52(m, 1H), 6.83-6.69(m, 2H), 5.03(d, 1H, J=14 Hz), 5.02(s, 1H), 4.56(d, 1H, J=14 Hz), 4.03-3.97(m, 1H), 2.59(d, 1H, J=5.3 Hz), and 1.26(d, 3H, J=6.6 Hz)

EXAMPLE 15

Synthesis of (2R, 3R)-2-(2,4-difluorophenyl)-1-(1H-1,2,4-triazol-1-yl)-2,3-butanediol

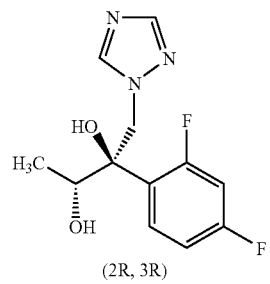

(2R, 3R)

The (2R, 3R)-3-(tert-butyldimethylsilyloxy)-2-(2,4-difluorophenyl)-1-(1H-1,2,4-triazol-1-yl)-2-butanol (2.0 g, 5.22 mmol) synthesized in Example 12 was dissolved in tetrahydrofuran (20 g). Tetra-n-butyl-ammonium fluoride (2.05 g, 7.83 mmol) was added to the solution and the mixture was stirred at room temperature for 30 minutes. Water (20 g) and ethyl acetate (40 g) were added to the reaction mixture and the mixture was stirred for 10 minutes. Subsequently, an organic layer was separated. The organic layer was dried with anhydrous magnesium sulfate. The drying agent was filtered and the filtrate was concentrated under reduced pressure. The resultant light yellow syrup was crystallized with toluene to recover white crystals of the target compound (1.31 g, 94%). Melting point: 116° C. to 117° C., Optical purity: 99% ee, Diastereomeric excess: 99.5% de Analytical conditions/YMC-PACK ODS A-303, Eluent composition: methanol:water:acetic acid=70:30:0.2, Detection method: UV 254 nm $^1$H-N.M.R. (270 MHz, CDCl$_3$): δ=7.84(s, 1H), 7.82(s, 1H), 7.46-7.37(m, 1H), 6.80-6.72(m, 2H), 4.87-4.77(m, 3H), 4.36-4.29(m, 1H), 2.63(d, 1H, J=9.2 Hz), and 0.97(d, 3H, J=6.5 Hz)

EXAMPLE 16

Synthesis of (2R, 3R)-2-(2,4-difluorophenyl)-1-(1H-1,2,4-triazol-1-yl)-2,3-butanediol

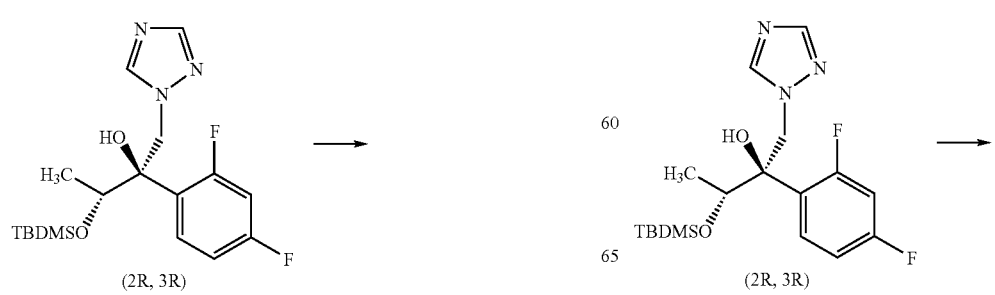

(2R, 3R)             (2R, 3R)

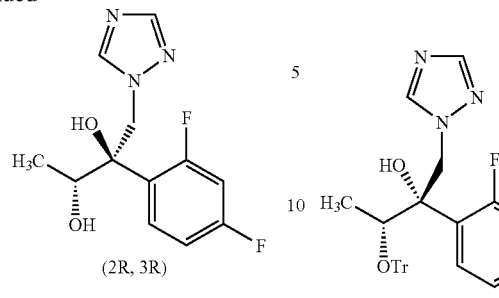

(2R, 3R)

The (2R, 3R)-3-(tert-butyldimethylsilyloxy)-2-(2,4-difluorophenyl)-1-(1H-1,2,4-triazol-1-yl)-2-butanol (12.2 g) synthesized in Example 12 was dissolved in methanol (41 mL). Hydrochloric acid (3 N, 21 g) was added to the solution and the mixture was stirred at 50° C. for four hours. Toluene (120 g) was added to the reaction mixture and was then stirred. Subsequently, an aqueous layer was separated. An aqueous solution (2 N, 41 g) of sodium hydroxide was added to the aqueous layer so that the pH of the mixture was controlled to be 9. The target compound was extracted with ethyl acetate (120 mL). The extracted organic layer was dried with anhydrous magnesium sulfate. The drying agent was filtered, and the filtrate was concentrated under reduced pressure. The resultant light yellow syrup was crystallized with toluene to recover-white crystals of the target compound (7.9 g, 92%). The values of the physical properties corresponded with those in Example 15. Diastereomeric excess: 99.5% de

EXAMPLE 17

Synthesis of (2R, 3R)-2-(2,4-difluorophenyl)-1-(1H-1,2,4-triazol-1-yl)-2,3-butanediol and (2S, 3R)-2-(2,4-difluorophenyl)-1-(1H-1,2,4-triazol-1-yl)-2,3-butanediol

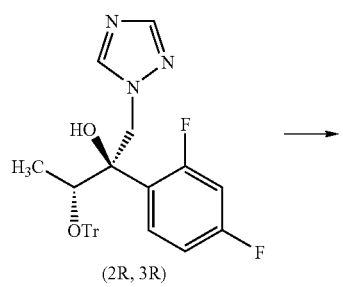

(2R, 3R)

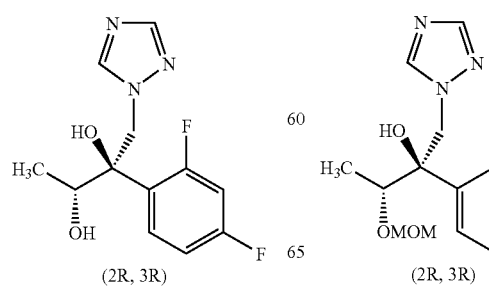

(2R, 3R)

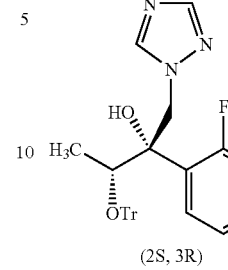

(2S, 3R)

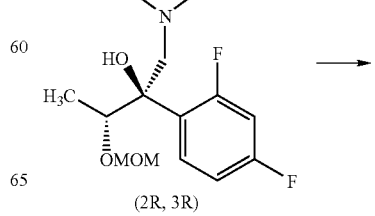

(2S, 3R)

The mixture (225 mg, 0.5 mmol) of (2R, 3R)-2-(2,4-difluorophenyl)-3-(methoxymethyloxy)-1-(1H-1,2,4-triazol-1-yl)-2-butanol and (2S, 3R) (2R, 3R)-2-(2,4-difluorophenyl)-3-(methoxymethyloxy)-1-(1H-1,2,4-triazol-1-yl)-2-butanol synthesized in Example 7 was treated as in Example 16 to recover the target compound (121 mg, 90%), which was a mixture of diastereomers. The ratio of the diastereomers was (2R, 3R):(2S, 3R)=4.3:1.

Analytical conditions/YMC-PACK ODS A-303, Eluent composition: methanol:water:acetic acid=70:30:0.2, Detection method: UV 254 nm The spectral data of $^1$H-N.M.R. corresponded with those in Examples 15 and 16.

EXAMPLE 18

Synthesis of (2R, 3R)-2-(2,4-difluorophenyl)-1-(1H-1,2,4-triazol-1-yl)-2,3-butanediol and (2S, 3R)-2-(2,4-difluorophenyl)-1-(1H-1,2,4-triazol-1-yl)-2,3-butanediol

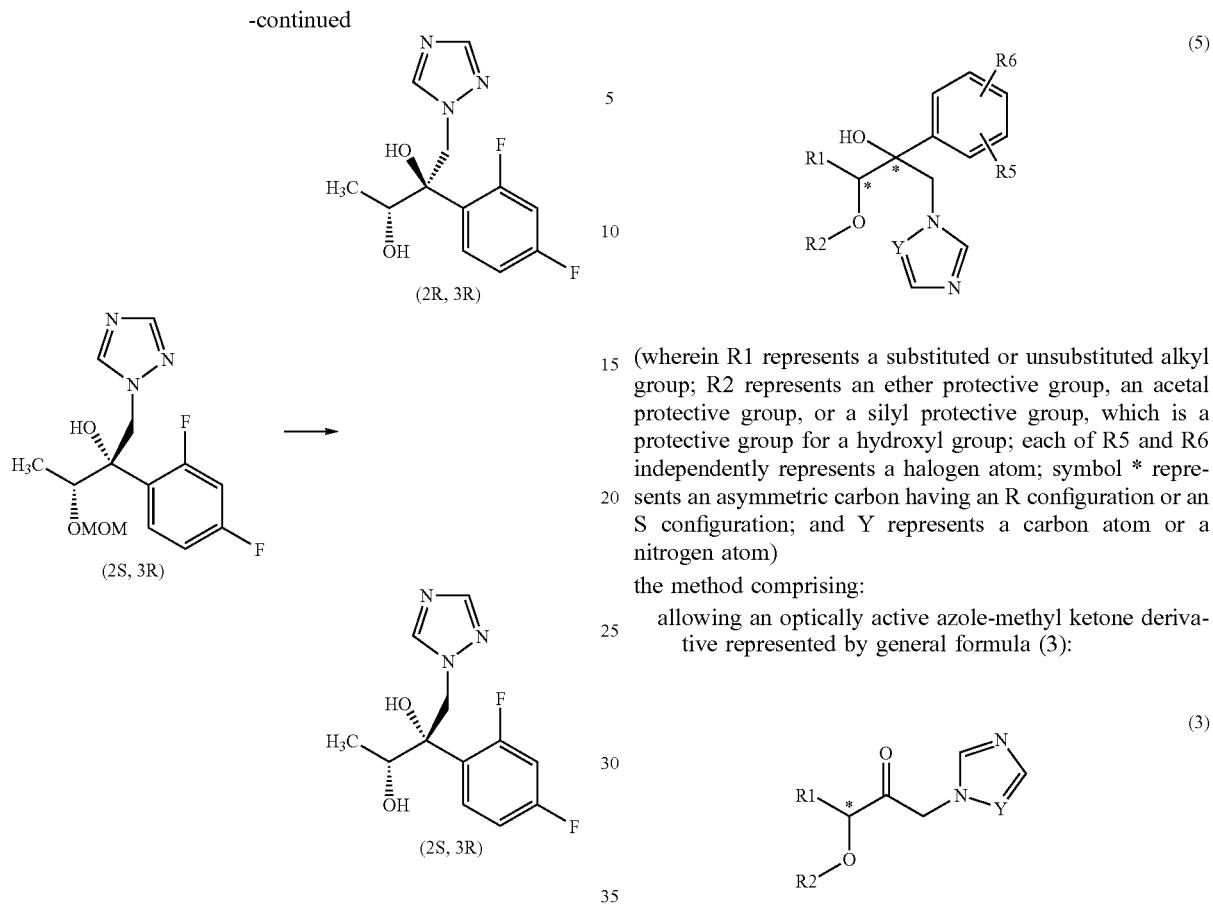

(2R, 3R)

(2S, 3R)

(2S, 3R)

The mixture (38 mg, 0.121 mmol) of (2R, 3R)-2-(2,4-difluorophenyl)-3-(methoxymethyloxy)-1-(1H-1,2,4-triazol-1-yl)-2-butanol and (2S, 3R)-2-(2,4-difluorophenyl)-3-(methoxymethyloxy)-1-(1H-1,2,4-triazol-1-yl)-2-butanol synthesized in Example 10 was treated as in Example 16 to recover the target compound (28 mg, 85%), which was a mixture of diastereomers. The ratio of the diastereomers was (2R, 3R):(2S, 3R)=6:1.

Analytical conditions/YMC-PACK ODS A-303, Eluent composition: methanol:water:acetic acid=70:30:0.2, Detection method: UV 254 nm The spectral data of $^1$H-N.M.R. corresponded with those in Examples 15 and 16.

INDUSTRIAL APPLICABILITY

The present invention provides a new method for producing a new, optically active azole alkyl ketone derivative and a new, optically active azole-methyl alcohol derivative, which are significantly important intermediates of medicines and agricultural chemicals. Furthermore, the present invention provides a stable method for inexpensively producing an optically active 2-phenyl-2,3,-dihydroxypropyl azole derivative by simple steps.

The invention claimed is:

1. A method for producing an optically active azole-methyl alcohol derivative represented by general formula (5):

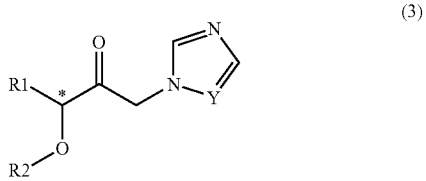

(wherein R1 represents a substituted or unsubstituted alkyl group; R2 represents an ether protective group, an acetal protective group, or a silyl protective group, which is a protective group for a hydroxyl group; each of R5 and R6 independently represents a halogen atom; symbol * represents an asymmetric carbon having an R configuration or an S configuration; and Y represents a carbon atom or a nitrogen atom)

the method comprising:

allowing an optically active azole-methyl ketone derivative represented by general formula (3):

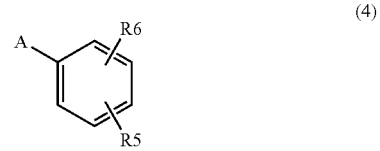

(wherein R1, R2, Y, and symbol * are as defined above) to diastereoselectively react with a phenyl metallic reagent represented by general formula (4):

(4)

A—⟨R6/R5⟩

(wherein R5 and R6 are as defined above; A represents Li, MgX, ZnX, TiX$_3$, Ti(OR7)$_3$, CuX, or CuLi, {wherein X represents a halogen atom, and R7 represents a substituted or unsubstituted alkyl group}).

2. The method according to claim 1 wherein R1 is a methyl group, and each of R5 and R6 is a fluorine or chlorine atom.

3. A method according to claim 1, wherein the optically active azole-methyl ketone derivative represented by general formula (3) is allowed to anti-selectively with the phenyl metallic reagent represented by general formula (4).

4. The method according to claim 3 wherein R1 is a methyl group, and each of R5 and R6 is a fluorine or chlorine atom.

5. The method according to claim 1, wherein the optically active azole-methyl ketone derivative represented by general formula (3) is allowed to syn-selectively react with the phenyl metallic reagent represented by general formula (4).

6. The method according to claim 5 wherein R1 is a methyl group, and each of R5 and R6 is a fluorine or chlorine atom.

7. An optically active azole-methyl alcohol derivative represented by general formula (5):

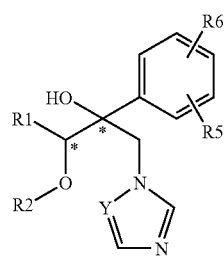

(5)

(wherein R1 represents a substituted or unsubstituted alkyl group; R2 is a silyl protective group; each of R5 and R6 independently represents a halogen atom; symbol * represents an asymmetric carbon having an R configuration or an S configuration; and Y represents a carbon atom or a nitrogen atom.

8. The optically active azole-methyl alcohol derivative according to claim 7, wherein R1 is a methyl group.

9. The optically active azole-methyl alcohol derivative according to claim 7, wherein each of R5 and R6 is a flourine or chlorine atom.

10. The optically active azole-methyl alcohol derivative according to claim 7, wherein Y is a nitrogen atom.

11. The optically active azole-methyl alchol derivative according to claim 7, wherein R2 is one selected from the group consisting of trimethylsilyl, triethylsilyl, tert-butyldimethylsilyl, and tert-butyldiphenylsilyl groups.

12. The method according to claim 1, wherein R2 is one selected from the group consisting of methyl, ethyl, tert-butyl, octyl, allyl, benzyl, p-methoxybenzyl, fluorenyl, trityl, benzhydryl, methoxymethyl, ethoxyethyl, methoxyethoxymethyl, tetrahydropyranyl, tetrahydrofuranyl, trimethylsilyl, triethylsilyl, tert-butyldimethylsilyl, and tert-butyldiphenylsilyl groups.

13. The method according to claim 2, wherein R2 is one selected from the group consisting of methyl, ethyl, tert-butyl, octyl, allyl, benzyl, p-methoxybenzyl, fluorenyl, trityl, benzhydryl, methoxymethyl, ethoxyethyl, methoxyethoxymethyl, tetrahydropyranyl, tetrahydrofuranyl, trimethylsilyl, triethylsilyl, tert-butyldimethylsilyl, and tert-butyldiphenylsilyl groups.

14. The method according to claim 3, wherein R2 is one selected from the group consisting of methyl, ethyl, tert-butyl, octyl, allyl, benzyl, p-methoxybenzyl, fluorenyl, trityl, benzhydryl, methoxymethyl, ethoxyethyl, methoxyethoxymethyl, tetrahydropyranyl, tetrahydrofuranyl, trimethylsilyl, triethylsilyl, tert-butyldimethylsilyl, and tert-butyldiphenylsilyl groups.

15. The method according to claim 5, wherein R2 is one selected from the group consisting of methyl, ethyl, tert-butyl, octyl, allyl, benzyl, p-methoxybenzyl, fluorenyl, trityl, benzhydryl, methoxymethyl, ethoxyethyl, methoxyethoxymethyl, tetrahydropyranyl, tetrahydrofuranyl, trimethylsilyl, triethylsilyl, tert-butyldimethylsilyl, and tert-butyldiphenylsilyl groups.

16. The method according to claim 1, wherein the azole-methyl ketone derivative represented by general formula (3) is obtained by the method comprising:

allowing an α-hydroxycarboxylic acid derivative represented by general formula (1):

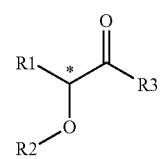

(1)

(wherein R1, R2, and symbol * are as defined in claim 1 and R3 represents a hydroxyl group, a halogen atom, a substituted or unsubstituted acyl group, a substituted or unsubstituted carbonate group, a substituted or unsubstituted alkyloxy group, a substituted or unsubstituted aralkyloxy group, a substituted or unsubstituted phenoxy group, or a substituted or unsubstituted amino group)

to react with an azole acetic acid derivative represented by general formula (2):

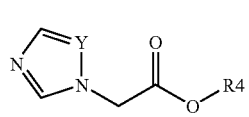

(2)

(wherein R4 represents a hydrogen atom, a substituted or unsubstituted alkyl group, an alkali metal, or an alkaline earth metal salt; and Y is as defined in claim 1) under a basic condition.

17. The method according to claim 16 wherein R1 is a methyl group.

18. A method for producing an optically active 2-phenyl-2,3-dihydroxypropyl azole derivative represented by general formula (6):

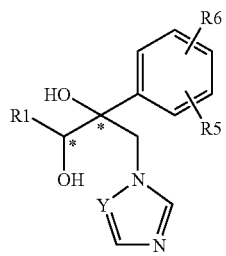

(6)

(wherein R1, R5, R6 and symbol * represents the same as defined in claim 1), said method comprising:

selectively deprotecting the protective group R2 for a hydroxyl group of the optically active azole-methyl alcohol derivative represented by general formula (5) obtained by the method as claimed in claims 1.

* * * * *